US007897568B2

(12) United States Patent
Jia et al.

(10) Patent No.: US 7,897,568 B2
(45) Date of Patent: Mar. 1, 2011

(54) COMPOSITIONS FOR TREATMENT OF CANCER

(75) Inventors: Zongchao Jia, Kingston (CA); Vinay K. Singh, Kingston (CA)

(73) Assignees: Vinay K. Singh, Kingston, Ontario (CA); Zongchao Jia, Kingston, Ontario (CA)

( * ) Notice: Subject to any disclaimer, the term of this patent is extended or adjusted under 35 U.S.C. 154(b) by 184 days.

(21) Appl. No.: 11/682,070

(22) Filed: Mar. 5, 2007

(65) Prior Publication Data
US 2007/0238667 A1 Oct. 11, 2007

Related U.S. Application Data

(60) Provisional application No. 60/778,713, filed on Mar. 3, 2006.

(51) Int. Cl.
*A61K 38/00* (2006.01)
(52) U.S. Cl. .............. 514/12; 514/13; 514/14; 514/15; 530/324; 530/325; 530/326; 530/327; 530/328
(58) Field of Classification Search ............ None
See application file for complete search history.

(56) References Cited

U.S. PATENT DOCUMENTS

| 6,225,086 | B1 | 5/2001 | Morrow et al. ............. 435/69.1 |
| 7,008,778 | B1 | 3/2006 | Ji et al. .................... 435/69.1 |
| 7,071,309 | B2 | 7/2006 | Ji et al. .................... 530/387.1 |
| 7,417,130 | B2 | 8/2008 | Stumpp et al. ............. 536/23.1 |
| 2004/0146935 | A1 | 7/2004 | Roberts et al. .............. 435/7.1 |
| 2007/0054268 | A1 | 3/2007 | Sutherland et al. ............ 435/6 |
| 2007/0172462 | A1 | 7/2007 | Bohn et al. ................ 424/93.2 |

FOREIGN PATENT DOCUMENTS

| WO | 00/34330 | * | 6/2000 |
| WO | 02/20565 | A2 | 3/2002 |
| WO | 2004/022778 | * | 3/2004 |
| WO | 2006/063397 | | 6/2005 |
| WO | 2005/068661 | | 7/2005 |

OTHER PUBLICATIONS

Freshney (Culture of Animal Cells, A Manual of Basic Technique, Alan R. Liss, Inc., 1983, New York, p4).*
Dermer (Bio/Technology, 1994, 12:320).*
Gura (Science, 1997, 278:1041-1042).*
Jain (Sci. Am., 1994, 271:58-65).*
Burgess et al, Journal of Cell Biology vol. 111 Nov. 1990 2129-2138.*
Lazar et al Molecular and Cellular Biology Mar. 1988 vol. 8 No. 3 1247-1252.*
Blajeski et al., "G1 and G2 cell-cycle arrest following microtubule depolymerization in human breast cancer cells", J. Clin. Invest.2002 110(1):91-99.

Bruening et al., "Synucleins Are Expressed in the Majority of Breast and Ovarian Carcinomas and in Preneoplastic Lesions of the Ovary", Cancer 2000 88:2154-2163.
Chan et al., "Prospective Randomized Trial of Docetaxel Versus Doxorubicin in Patients With Metastatic Breast Cancer", J. Clin. Oncol 1999 17(8):2341-2354.
Choy et al., , "Probing Residual Interactions in Unfolded Protein States Using NMR Spin Relaxation Techniques:An Application to Delta131Delta", J. Am. Chem. Soc. 2003 125:11988-11992.
Clayton, D.F. and George, J.M. "The synucleins:a family of proteins involved in synaptic function, plasticity, neurodegeneration and disease", Trends Neurosci. 1998 21(6):249-254.
Engelender et al., "Synphilin-1 associates with alpha-synuclein and promotes the formation of cytosolic inclusions", Nature Genetics 1999 22:110-114.
Elirzer et al., "Conformational Properties of alpha-Synuclein in its Free and Lipid-associated States", J. Mol. Biol. 2001 307:1061-1073.
Gupta et al., "Breast cancer-specific gene 1 interacts with the mitotic checkpoint kinse BubR1", Oncogene 2003 22:7593-7599.
Iakoucheva et al., "Intrinsic Disorder in Cell-signaling and Cancer-associated Proteins", J. Mol. Biol. 2002 323:573-584.
Inaba et al., "Synuclein gamma inhibits the mitotic checkpoint function and promotes chromosomal instability of breast cancer cells", Breast Cancer Res. Treat. 2005 94:25-35.
Ji et al., "Identification of a Breast Cancer-specific Gene, BCSG1, by Direct Differential cDNA Sequencing", Cancer Res. 1997 57:759-764.
Jia et al., "Stimulation of Breast Cancer Invasion and Metastasis by Synuclein gamma", Cancer Res. 1999 59:742-747.
Jiang et al., "Stimulation of Estrogen Receptor Signaling by gamma Synuclein", Cancer Res. 2003 63:3899-3903.
Jiang et al., "Gamma Synuclein, a Novel Heat-Shock Protein-Associated Chaperone, Stimulates Ligand-Dependent Estrogen Receptor alpha Signaling and Mammary Tumorigenesis", Cancer Res. 2004 64:4539-4546.
Kohl et al., "Designed to be stable:Crystal structure of a consensus ankyrin repeat protein", Proc. Natl. Acad. Sci. USA 2003 100(4):1700-1705.
Lavedan et al., "Identification, localization and characterization of the human gamma-synuclein gene", Hum Genet 1998 103:106-112.

(Continued)

*Primary Examiner*—Sheela J Huff
(74) *Attorney, Agent, or Firm*—Licata & Tyrrell P.C.

(57) ABSTRACT

Synthetic peptides containing an ankyrin repeat-like motif or portion thereof and mimetics thereof which interact with synuclein-gamma (SNCG) and reduce SNCG-mediated resistance of SNCG-expressing cancer cells to treatment with anticancer drugs or inhibit tumorigenesis and cancer cell proliferation are provided. Compositions containing these peptides, portions thereof or mimetics thereof are also provided. Methods for use of these peptides or portions thereof, compositions, and mimetics thereof in potentiating efficacy of anticancer drugs, in particular microtubule inhibitors and hormonal cancer therapies, and in treating cancer are also provided.

16 Claims, 11 Drawing Sheets

OTHER PUBLICATIONS

Liu et al., "Transcriptional suppression of synuclein gamma (SNCG) expression in human breast cancer cells by the growth inhibitory cytokine oncostatin M", Breast Cancer Res. Treat. 2000 62:99-107.

Liu et al. "Loss of Epigenetic Control of Synuclein-gamma Gene as a Molecular Indicator of Metastasis in a Wide Range of Human Cancers", Cancer Res. 2005 65(17):7635-7643.

Lu et al., "Blockade of API Transactivation Abrogates the Abnormal Expression of Breast Cancer-specific Gene 1 in Breast Cancer Cells", J. Biol. Chem. 2002 277(35):31364-31372.

Mosavi et al., "The ankyrin repeat as molecular architecture for protein recognition", Protein Science 2004 13:1435-1448.

Mosavi et al., "Consensus-derived structural determinants of the ankyrin repeat motif", Proc. Natl. Acad. Sci. USA 2002 99(25):16029-16034.

Pan et al., "Gamma-Synuclein Promotes Cancer Cell Survival and Inhibits Stress- and Chemotherapy Drug-induced Apoptosis by Modulating MAPK Pathways", J. Biol. Chem 2002 277(38):35050-35060.

Romero et al., "Natively Disordered Proteins—Functions and Predictions", . Appl. Bioinformatics 2004 3(2-3):105-113.

Shin et al., "Dual roles of human BubR1, a mitotic checkpoint kinase, in the monitoring of chromosomal instability", Cancer Cell 2003 4:483-497.

Singh, V.K., et al., (2005) "You do not need to have 'shape' to get recognized: Story of natively unfolded gamma-synuclein interaction with ankyrin repeat", FEBS Journal 272(sI): Abstract No. c6-006.

Tompa P., "Intrinsically unstructured proteins", Trends Biochem. Sci. 2002 27(10):527-533.

Uversky V.N., "Natively unfolded proteins:A point where biology waits for physics", Protein Sci. 2002 11:739-756.

Uversky et al., "Showing your ID:intrinsic disorder as an ID for recognition, regulation and cell signaling", J. Mol. Recognit. 2005 18:343-384.

Valero et al., "A Phase II Study of Docetaxel in Patients With Paclitaxel-Resistant Metastatic Breast Cancer", J. Clin. Oncol. 1998 16(10):3362-3368.

Wright et al., "Intrinsically Unstructured Proteins:Re-assessing the Protein Structure-Function Paradigm", J. Mol. Biol. 1999 293:321-331.

Wu et al., "Stage-specific Expression of Breast Cancer-specific Gene gamma-Synuclein", Cancer Epidemiol. Biomarkers Prev. 2003 12:920-925.

Yao et al., "NMR Stuctural and Dynamic Characterization of the Acid-Unfolded State of Apomyoglobin Provides Insights into the Early Events in Protein Folding", Biochemistry 2001 40:3561-3571.

International Preliminary Report on Patentability dated Sep. 18, 2008.

* cited by examiner

| pCI-SNCG:    | + | + | + | + |
| ------------ | - | - | - | - |
| pMT-BubR1:   | + | + | + | + |
| pEGFP-ANK:   | + | − | + | − |
| pEGFP:       | − | + | − | + |

|            | IP | Total lysates |
| ---------- | -- | ------------- |
| α-BubR1    |    |               |
| α-GFP      |    |               |
| α-SNCG     |    |               |

Figure 6

```
                         SEQUENCE LISTING

<160> NUMBER OF SEQ ID NOS: 32

<210> SEQ ID NO 1
<211> LENGTH: 34
<212> TYPE: PRT
<213> ORGANISM: Artificial sequence
<220> FEATURE:
<223> OTHER INFORMATION: Synthetic

<400> SEQUENCE: 1

Lys Gly Asn Ser Ala Leu His Val Ala Ser Gln His Gly His Leu Gly
1               5                   10                  15

Cys Ile Gln Thr Leu Val Arg Tyr Gly Ala Asn Val Thr Met Gln Asn
            20                  25                  30

His Gly

<210> SEQ ID NO 2
<211> LENGTH: 12
<212> TYPE: PRT
<213> ORGANISM: Artificial sequence
<220> FEATURE:
<223> OTHER INFORMATION: Synthetic

<400> SEQUENCE: 2

Gly Asn Ser Ala Leu His Val Ala Ser Gln His Gly
1               5                   10

<210> SEQ ID NO 3
<211> LENGTH: 18
<212> TYPE: PRT
<213> ORGANISM: Artificial sequence
<220> FEATURE:
<223> OTHER INFORMATION: Synthetic

<400> SEQUENCE: 3

Leu His Val Ala Ser Gln His Gly His Leu Gly Cys Ile Gln Thr Leu
1               5                   10                  15

Val Arg

<210> SEQ ID NO 4
<211> LENGTH: 13
<212> TYPE: PRT
```

-continued

```
<213> ORGANISM: Artificial sequence
<220> FEATURE:
<223> OTHER INFORMATION: Synthetic

<400> SEQUENCE: 4

His Leu Gly Cys Ile Gln Thr Leu Val Arg Tyr Gly Ala
1               5                   10

<210> SEQ ID NO 5
<211> LENGTH: 8
<212> TYPE: PRT
<213> ORGANISM: Artificial sequence
<220> FEATURE:
<223> OTHER INFORMATION: Synthetic

<400> SEQUENCE: 5

Gly Ala Asn Val Thr Met Gln Asn
1               5

<210> SEQ ID NO 6
<211> LENGTH: 4
<212> TYPE: PRT
<213> ORGANISM: Artificial sequence
<220> FEATURE:
<223> OTHER INFORMATION: Synthetic

<400> SEQUENCE: 6

Thr Pro Leu His
1

<210> SEQ ID NO 7
<211> LENGTH: 25
<212> TYPE: PRT
<213> ORGANISM: Artificial sequence
<220> FEATURE:
<223> OTHER INFORMATION: Synthetic
<220> FEATURE:
<221> NAME/KEY: VARIANT
<222> LOCATION: (2)..(2)
<223> OTHER INFORMATION: X=G, A, V, L, I, M, F, W, P or N
<220> FEATURE:
<221> NAME/KEY: VARIANT
<222> LOCATION: (3)..(3)
<223> OTHER INFORMATION: X=S, T, C, Y, N or Q
<220> FEATURE:
<221> NAME/KEY: VARIANT
<222> LOCATION: (4)..(4)
<223> OTHER INFORMATION: X=G, A, V, L, I, M, F, W or P
<220> FEATURE:
<221> NAME/KEY: VARIANT
<222> LOCATION: (7)..(7)
<223> OTHER INFORMATION: X=X=G, A, V, L, I, M, F, W, P or Q
<220> FEATURE:
<221> NAME/KEY: VARIANT
<222> LOCATION: (9)..(9)
<223> OTHER INFORMATION: X=G, A, V, L, I, M, F, W, P, S, T, C, Y, N or
      Q
<220> FEATURE:
<221> NAME/KEY: VARIANT
<222> LOCATION: (10)..(10)
<223> OTHER INFORMATION: X= S, T, C, Y, N, Q or K
<220> FEATURE:
<221> NAME/KEY: VARIANT
<222> LOCATION: (11)..(11)
<223> OTHER INFORMATION: X= S, T, C, Y, N, Q or V
<220> FEATURE:
<221> NAME/KEY: VARIANT
<222> LOCATION: (14)..(14)
<223> OTHER INFORMATION: X=G, A, V, L, I, M, F, W, P or K
<220> FEATURE:
<221> NAME/KEY: VARIANT
<222> LOCATION: (15)..(15)
<223> OTHER INFORMATION: X=D, E, K, R or H
```

```
<220> FEATURE:
<221> NAME/KEY: VARIANT
<222> LOCATION: (16)..(16)
<223> OTHER INFORMATION: X=I or C
<220> FEATURE:
<221> NAME/KEY: VARIANT
<222> LOCATION: (17)..(17)
<223> OTHER INFORMATION: X=G, A, V, L, I, M, F, W or P
<220> FEATURE:
<221> NAME/KEY: VARIANT
<222> LOCATION: (18)..(18)
<223> OTHER INFORMATION: X=G, A, V, L, I, M, F, W, P, S, T, C, Y, N,
      Q or R
<220> FEATURE:
<221> NAME/KEY: VARIANT
<222> LOCATION: (19)..(19)
<223> OTHER INFORMATION: X=G, A, V, L, I, M, F, W, P, K, R or H
<220> FEATURE:
<221> NAME/KEY: VARIANT
<222> LOCATION: (21)..(21)
<223> OTHER INFORMATION: X=G, A, V, L, I, M, F, W, P or T
<220> FEATURE:
<221> NAME/KEY: VARIANT
<222> LOCATION: (22)..(22)
<223> OTHER INFORMATION: X=S, T, C, Y, N, Q, D, E or R
<220> FEATURE:
<221> NAME/KEY: VARIANT
<222> LOCATION: (23)..(23)
<223> OTHER INFORMATION: X=G, A, V, L, I, M, F, W, P, S, T, C, Y, N,
      Q or E

<400> SEQUENCE: 7

Gly Xaa Xaa Xaa Leu His Xaa Ala Xaa Xaa Xaa Gly His Xaa Xaa Xaa
1               5                   10                  15

Xaa Xaa Xaa Leu Xaa Xaa Xaa Gly Ala
            20                  25

<210> SEQ ID NO 8
<211> LENGTH: 33
<212> TYPE: PRT
<213> ORGANISM: Artificial sequence
<220> FEATURE:
<223> OTHER INFORMATION: Synthetic

<400> SEQUENCE: 8

Asn Gly Asn Asn Leu Leu His Ile Ala Ala Ser Gln Gly His Ala His
1               5                   10                  15

Cys Leu Gln His Leu Thr Ser Leu Met Gly Glu Asp Cys Leu Asn Glu
            20                  25                  30

Arg

<210> SEQ ID NO 9
<211> LENGTH: 33
<212> TYPE: PRT
<213> ORGANISM: Artificial sequence
<220> FEATURE:
<223> OTHER INFORMATION: Synthetic

<400> SEQUENCE: 9

Lys Lys Leu Thr Pro Ala Gly Leu Ala Ile Lys Asn Gly Gln Leu Glu
1               5                   10                  15

Cys Val Arg Trp Met Val Ser Glu Thr Glu Ala Ile Ala Glu Leu Ser
            20                  25                  30

Cys

<210> SEQ ID NO 10
<211> LENGTH: 33
<212> TYPE: PRT
```

<210> ORGANISM: Artificial sequence
<220> FEATURE:
<223> OTHER INFORMATION: Synthetic

<400> SEQUENCE: 10

Asp Glu Pro Ser Leu Ile His Val Ala Gly Cys Val Gly Gln Lys Lys
1               5                   10                  15
Ile Leu Leu Trp Leu Leu Gln Phe Met Gln Glu Gln Gly Ile Ser Leu
            20                  25                  30
Asp

<210> SEQ ID NO 11
<211> LENGTH: 33
<212> TYPE: PRT
<213> ORGANISM: Artificial sequence
<220> FEATURE:
<223> OTHER INFORMATION: Synthetic

<400> SEQUENCE: 11

Asp Gly Asn Ser Ala Val His Val Ala Ser Gln His Gly Tyr Leu Gly
1               5                   10                  15
Cys Ile Gln Thr Leu Val Glu Tyr Gly Ala Asn Val Thr Met Gln Asn
            20                  25                  30
His

<210> SEQ ID NO 12
<211> LENGTH: 29
<212> TYPE: DNA
<213> ORGANISM: Artificial sequence
<220> FEATURE:
<223> OTHER INFORMATION: Synthetic

<400> SEQUENCE: 12
gcggatccat ggatgtcttc aagaagggc                                    29

<210> SEQ ID NO 13
<211> LENGTH: 32
<212> TYPE: DNA
<213> ORGANISM: Artificial sequence
<220> FEATURE:
<223> OTHER INFORMATION: Synthetic

<400> SEQUENCE: 13
gagcggccgc agtctccccc actctgggcc tc                                32

<210> SEQ ID NO 14
<211> LENGTH: 93
<212> TYPE: DNA
<213> ORGANISM: Artificial sequence
<220> FEATURE:
<223> OTHER INFORMATION: Synthetic

<400> SEQUENCE: 14
gcccttcacg tagcctcaca gcatggccac cttggatgca tacagacctt ggttagatat    60
ggagcaaatg tcaccatgca gaaccacggg tga                                93

<210> SEQ ID NO 15
<211> LENGTH: 19
<212> TYPE: DNA
<213> ORGANISM: Artificial sequence
<220> FEATURE:
<223> OTHER INFORMATION: Synthetic

<400> SEQUENCE: 15
aagggcaaca gtgcccttc                                                    19

<210> SEQ ID NO 16
<211> LENGTH: 19
<212> TYPE: DNA
<213> ORGANISM: Artificial sequence
<220> FEATURE:
<223> OTHER INFORMATION: Synthetic

<400> SEQUENCE: 16
tcacccgtgg ttctgcatg                                                    19

<210> SEQ ID NO 17
<211> LENGTH: 42
<212> TYPE: DNA
<213> ORGANISM: Artificial sequence
<220> FEATURE:
<223> OTHER INFORMATION: Synthetic

<400> SEQUENCE: 17
caccttggat gcatacagac cttggttaga tatggagcat ga                          42

<210> SEQ ID NO 18
<211> LENGTH: 18
<212> TYPE: DNA
<213> ORGANISM: Artificial sequence
<220> FEATURE:
<223> OTHER INFORMATION: Synthetic

<400> SEQUENCE: 18
caccttggat gcatacag                                                     18

<210> SEQ ID NO 19
<211> LENGTH: 19
<212> TYPE: DNA
<213> ORGANISM: Artificial sequence
<220> FEATURE:
<223> OTHER INFORMATION: Synthetic

<400> SEQUENCE: 19
tcatgctcca tatctaacc                                                    19

<210> SEQ ID NO 20
<211> LENGTH: 57
<212> TYPE: DNA
<213> ORGANISM: Artificial sequence
<220> FEATURE:
<223> OTHER INFORMATION: Synthetic

<400> SEQUENCE: 20
cttcacgtag cctcacagca tggccacctt ggatgcatac agaccttggt tagatga          57

<210> SEQ ID NO 21
<211> LENGTH: 19
<212> TYPE: DNA
<213> ORGANISM: Artificial sequence
<220> FEATURE:
<223> OTHER INFORMATION: Synthetic

<400> SEQUENCE: 21
cttcacgtag cctcacagc                                                    19

<210> SEQ ID NO 22
<211> LENGTH: 18
<212> TYPE: DNA

<210> SEQ ID NO 22
<211> LENGTH: 18
<212> TYPE: DNA
<213> ORGANISM: Artificial sequence
<220> FEATURE:
<223> OTHER INFORMATION: Synthetic

<400> SEQUENCE: 22
tcatctaacc aaggtctg                                                    18

<210> SEQ ID NO 23
<211> LENGTH: 39
<212> TYPE: DNA
<213> ORGANISM: Artificial sequence
<220> FEATURE:
<223> OTHER INFORMATION: Synthetic

<400> SEQUENCE: 23
ggcaacagtg cccttcacgt agcctcacag catggctga                             39

<210> SEQ ID NO 24
<211> LENGTH: 19
<212> TYPE: DNA
<213> ORGANISM: Artificial sequence
<220> FEATURE:
<223> OTHER INFORMATION: Synthetic

<400> SEQUENCE: 24
cttcacgtag cctcacagc                                                   19

<210> SEQ ID NO 25
<211> LENGTH: 18
<212> TYPE: DNA
<213> ORGANISM: Artificial sequence
<220> FEATURE:
<223> OTHER INFORMATION: Synthetic

<400> SEQUENCE: 25
tcagccatgc tgtgaggc                                                    18

<210> SEQ ID NO 26
<211> LENGTH: 27
<212> TYPE: DNA
<213> ORGANISM: Artificial sequence
<220> FEATURE:
<223> OTHER INFORMATION: Synthetic

<400> SEQUENCE: 26
ggagcaaatg tcaccatgca gaactga                                          27

<210> SEQ ID NO 27
<211> LENGTH: 31
<212> TYPE: DNA
<213> ORGANISM: Artificial sequence
<220> FEATURE:
<223> OTHER INFORMATION: Synthetic

<400> SEQUENCE: 27
aattggagca aatgtcacca tgcagaactg a                                     31

<210> SEQ ID NO 28
<211> LENGTH: 31
<212> TYPE: DNA
<213> ORGANISM: Artificial sequence
<220> FEATURE:
<223> OTHER INFORMATION: Synthetic

<400> SEQUENCE: 28
aatttcagtt ctgcatggtg acatttgctc c                                     31

```
<210> SEQ ID NO 29
<211> LENGTH: 12
<212> TYPE: PRT
<213> ORGANISM: Artificial sequence
<220> FEATURE:
<223> OTHER INFORMATION: Synthetic

<400> SEQUENCE: 29

Gly Tyr Gly Arg Lys Lys Arg Arg Gln Arg Arg Arg
1               5                  10

<210> SEQ ID NO 30
<211> LENGTH: 24
<212> TYPE: PRT
<213> ORGANISM: Artificial sequence
<220> FEATURE:
<223> OTHER INFORMATION: Synthetic

<400> SEQUENCE: 30

Gly Tyr Gly Arg Lys Lys Arg Arg Gln Arg Arg Arg Gly Asn Ser Ala
1               5                  10                  15

Leu His Val Ala Ser Gln His Gly
            20

<210> SEQ ID NO 31
<211> LENGTH: 20
<212> TYPE: PRT
<213> ORGANISM: Artificial sequence
<220> FEATURE:
<223> OTHER INFORMATION: Synthetic

<400> SEQUENCE: 31

Gly Tyr Gly Arg Lys Lys Arg Arg Gln Arg Arg Arg Gly Ala Asn Val
1               5                  10                  15

Thr Met Gln Asn
            20

<210> SEQ ID NO 32
<211> LENGTH: 32
<212> TYPE: PRT
<213> ORGANISM: Artificial sequence
<220> FEATURE:
<223> OTHER INFORMATION: Synthetic
<220> FEATURE:
<221> NAME/KEY: VARIANT
<222> LOCATION: (2)..(2)
<223> OTHER INFORMATION: X=G, A, V, L, I, M, F, W, P or N
<220> FEATURE:
<221> NAME/KEY: VARIANT
<222> LOCATION: (3)..(3)
<223> OTHER INFORMATION: X=S, T, C, Y, N or Q
<220> FEATURE:
<221> NAME/KEY: VARIANT
<222> LOCATION: (4)..(4)
<223> OTHER INFORMATION: X=G, A, V, L, I, M, F, W or P
<220> FEATURE:
<221> NAME/KEY: VARIANT
<222> LOCATION: (7)..(7)
<223> OTHER INFORMATION: X=G, A, V, L, I, M, F, W, P or Q
<220> FEATURE:
<221> NAME/KEY: VARIANT
<222> LOCATION: (9)..(9)
<223> OTHER INFORMATION: X=G, A, V, L, I, M, F, W, P, S, T, C, Y, N or
      Q
<220> FEATURE:
<221> NAME/KEY: VARIANT
<222> LOCATION: (10)..(10)
<223> OTHER INFORMATION: X=S, T, C, Y, N, Q or K
<220> FEATURE:
```

```
<221> NAME/KEY: VARIANT
<222> LOCATION: (11)..(11)
<223> OTHER INFORMATION: X=S, T, C, Y, N, Q or V
<220> FEATURE:
<221> NAME/KEY: VARIANT
<222> LOCATION: (14)..(14)
<223> OTHER INFORMATION: X=G, A, V, L, I, M, F, W, P or K
<220> FEATURE:
<221> NAME/KEY: VARIANT
<222> LOCATION: (15)..(15)
<223> OTHER INFORMATION: X=D, E, K, R or H
<220> FEATURE:
<221> NAME/KEY: VARIANT
<222> LOCATION: (16)..(16)
<223> OTHER INFORMATION: X=I or C
<220> FEATURE:
<221> NAME/KEY: VARIANT
<222> LOCATION: (17)..(17)
<223> OTHER INFORMATION: X=G, A, V, L, I, M, F, W or P
<220> FEATURE:
<221> NAME/KEY: VARIANT
<222> LOCATION: (18)..(18)
<223> OTHER INFORMATION: X=G, A, V, L, I, M, F, W, P, S, T, C, Y, N,
     Q or R
<220> FEATURE:
<221> NAME/KEY: VARIANT
<222> LOCATION: (19)..(19)
<223> OTHER INFORMATION: X=G, A, V, L, I, M, F, W, P, K, R or H
<220> FEATURE:
<221> NAME/KEY: VARIANT
<222> LOCATION: (21)..(21)
<223> OTHER INFORMATION: X=G, A, V, L, I, M, F, W, P or T
<220> FEATURE:
<221> NAME/KEY: VARIANT
<222> LOCATION: (22)..(22)
<223> OTHER INFORMATION: X= S, T, C, Y, N, Q, D, E or R
<220> FEATURE:
<221> NAME/KEY: VARIANT
<222> LOCATION: (23)..(23)
<223> OTHER INFORMATION: X=G, A, V, L, I, M, F, W, P, S, T, C, Y, N,
     Q or E
<220> FEATURE:
<221> NAME/KEY: VARIANT
<222> LOCATION: (26)..(26)
<223> OTHER INFORMATION: X=G, A, V, L, I, M, F, W, P, S, T, C, Y, N,
     Q or E
<220> FEATURE:
<221> NAME/KEY: VARIANT
<222> LOCATION: (27)..(27)
<223> OTHER INFORMATION: X=G, A, V, L, I, M, F, W, P, S, T, C, Y, N,
     Q or D
<220> FEATURE:
<221> NAME/KEY: VARIANT
<222> LOCATION: (29)..(29)
<223> OTHER INFORMATION: X=G, A, V, L, I, M, F, W, P, S, T, C, Y, N or
     Q
<220> FEATURE:
<221> NAME/KEY: VARIANT
<222> LOCATION: (30)..(30)
<223> OTHER INFORMATION: X=G, A, V, L, I, M, F, W, P, D or E
<220> FEATURE:
<221> NAME/KEY: VARIANT
<222> LOCATION: (31)..(31)
<223> OTHER INFORMATION: X=G, A, V, L, I, M, F, W, P, S, T, C, Y, N or
     Q
<220> FEATURE:
<221> NAME/KEY: VARIANT
<222> LOCATION: (32)..(32)
<223> OTHER INFORMATION: X=G, A, V, L, I, M, F, W, P, S, T, C, Y, N,
     Q or E

<400> SEQUENCE: 32

Gly Xaa Xaa Xaa Leu His Xaa Ala Xaa Xaa Gly His Xaa Xaa Xaa
1               5                   10                  15

Xaa Xaa Xaa Leu Xaa Xaa Xaa Gly Ala Xaa Xaa Asn Xaa Xaa Xaa Xaa
            20                  25                  30
```

COMPOSITIONS FOR TREATMENT OF CANCER

This patent application claims the benefit of priority from U.S. Provisional Application Ser. No. 60/778,713, filed Mar. 3, 2006, teachings of which are herein incorporated by reference in their entirety.

FIELD OF THE INVENTION

Synuclein-gamma (SNCG) plays an oncogenic role in carcinogenesis and is highly expressed in advanced and metastatic carcinomas. SNCG interacts with BubR1, a mitotic checkpoint kinase, resulting in inhibition of mitotic checkpoint control upon spindle damage and in resistance to anticancer drugs such as nocodazole and paclitaxel. SNCG is also a chaperone protein in the (Hsp)-based multiprotein chaperone complex for stimulation of ligand-dependent estrogen receptor (ER)-α signaling and stimulates hormone-responsive tumorigenesis. The present invention provides peptides comprising at least one ankyrin repeat-like motif or a portion thereof or a mimetic thereof which interact with SNCG and reduce SNCG-mediated resistance to treatment with anticancer drugs and SNCG-mediated tumorigenesis. The present invention also provides cell lines stably transfected to express these peptides, pharmaceutical compositions comprising these peptides, portions thereof or mimetics thereof and methods for their use in potentiating cancer treatments and inhibiting tumorigenesis and cancer cell proliferation.

BACKGROUND OF THE INVENTION

Breast cancer development and progression involve the abnormality of multiple genes through genetic and epigenetic alterations. By conducting differential DNA sequencing and in situ hybridization, the aberrant expression of synuclein-gamma (SNCG) (Lavedan et al. Hum Genet. 1998 103:106-112), also referred to as Breast Cancer Specific Gene 1 (breast cancerSG1)(Ji et al. Cancer Res. 1997 57:759-764), has been linked to the disease progression of breast cancer.

SNCG along with synuclein-alpha (SNCA) and synuclein-beta (SNCB) belong to a family of intrinsically disordered proteins (Uversky, V. N. Protein Sci. 2002 11:739-756). Intrinsically disordered proteins are partially or completely unfolded under physiological or non-denaturing conditions. Although often traditionally described as "random coil," many studies have shown disordered proteins to possess significant nonrandom structure, usually in the form of residual secondary structure (Elierzer et al. J. Mol. Biol. 2001 307: 1061-1073; Yao et al. Biochemistry 2001 40:3561-3571) and hydrophobic clustering (Choy et al. J. Am. Chem. Soc. 2003 125:11988-11992). The recent recognition that intrinsically disordered proteins are more common than previously thought and can play important biological roles has challenged the traditional protein structure-function paradigm, which holds that polypeptide chains require compact, globular structure in order to function (Wright, P. E. and Dyson, H. J J. Mol. Biol. 1999 293:321-331; Tompa, P. Trends Biochem. Sci. 2002 27:527-533; Uversky et al. J. Mol. Recognit. 2005 18:434-384).

SNCG mRNA and protein are not expressed in normal breast tissue or tissues with benign breast diseases but are abundantly expressed in a high percentage of invasive and metastatic breast carcinomas (Ji et al. Cancer Res. 1997 57:759-764; Bruening et al. Cancer 2000 88:2154-2163; Wu et al. Cancer Epidemiol. Biomarkers Prev. 2003 12:920-925).

A series of in vitro and in vivo functional studies have demonstrated that SNCG expression significantly stimulates proliferation (Liu et al. Breast Cancer Res. Treat. 2000 62:99-107; Lu et al. J. Biol. Chem. 2002 277:31364-31372; Jiang et al. Cancer Res. 2004 64:4539-4546; Jiang et al. Cancer Res. 2003 63:3899-3903), invasion and metastasis of breast cancer cells (Jia et al. Cancer Res. 1999 59:742-747).

SNCG has been shown to interact with BubR1, a mitotic checkpoint kinase required for the prevention of cell mitotic divisions following severe cell damage or mutation (Gupta et al. Oncogene 2003 22:7593-7599). The interaction of SNCG with BubR1 inhibits mitotic checkpoint control upon spindle damage and confers cellular resistance to anti-microtubule drugs such as nocodazole (Gupta et al. Oncogene 2003 22:7593-7599).

Nocodazole, a very commonly used inhibitor of microtubule assembly, experiences much reduced efficacy in SNCG-overexpressing MCF7 breast cancer cells, which is attributed to the SNCG-BubR1 interaction (Gupta et al. Oncogene 2003 22:7593-7599). The inhibitory effects of SNCG on checkpoint function are reduced when the cellular expression level of BubR1 is increased by ectopic over-expression (Inaba et al. Breast Cancer Res. Treat. 2005 94:25-35). Additional evidence shows that the interaction of BubR1 with CENP-E, which is critically required for mitotic checkpoint signaling, is impaired in the presence of SNCG, thereby suggesting that SNCG may inhibit BubR1 function by interfering with the BubR1 CENP-E interaction (Inaba et al. Breast Cancer Res. Treat. 2005 94:25-35). Taken together, these results suggest that BubR1 is a cellular target of natively unfolded SNCG, and the interaction of SNCG-BubR1 may represent a novel mechanism for inactivation of the mitotic checkpoint (Gupta et al. Oncogene 2003 22:7593-7599; Inaba et al. Breast Cancer Res. Treat. 2005 94:25-35).

Currently, microtubule inhibitors are used as first-line chemotherapeutic agents to treat patients with advanced or metastatic breast cancer (Valero et al. J. Clin. Oncol. 1998 16:3362-3368; Chan et al. J. Clin. Oncol. 1999 17:2341-2354). However, response rates to this class of drugs vary significantly. These microtubule-disrupting agents are believed to arrest cells in mitosis by triggering mitotic checkpoint activation, resulting in cells arrested in the mitotic phase without entering anaphase (Blajeski et al. J. Clin. Invest. 2002 110:91-99). Prolonged treatments with these agents lead to cell death by apoptosis (Shin et al. Cancer Cell 2003 4:483-497). Since the working mechanism of anti-microtubule drugs relies heavily on the normal function of the mitotic checkpoint machinery in which BubR1 is a critical component (Shin et al. Cancer Cell 2003 4:483-497), the inhibitory effect of SNCG on BubR1 function may be related to the induced resistance of breast cancer cells to microtubule inhibitors after exogenous expression of SNCG (Pan et al. J. Biol. Chem. 2002 277:35050-35060).

SNCG has also been disclosed to be a chaperone protein in the heat shock protein (Hsp)-based multiprotein complex for stimulation of ligand-dependent estrogen receptor (ER)-(signaling and stimulates hormone-responsive mammary and ovarian tumorigenesis (Jiang et al. Cancer Research 2004 64:4539-4546).

The ankyrin repeat, a 33 residue sequence motif, is one of the most frequently observed amino acid motifs in protein databases (Mosavi et al. Protein Science 2004 13:1435-1448). Twenty-four copies of this repeat are contained within the cytoskeletal protein ankyrin, hence its name. However, ankyrin repeats have been found in many proteins with a wide range of different functions.

SNCA, a protein with 55.9% sequence homology to SNCG, has been shown in a yeast two hybrid screen and in neurons to interact with synphilin-1, a protein containing several protein-protein interaction domains, such as ankyrin-like repeats and a coiled-coil domain (Engelender et al. Nat. Genet. 1999 22:110-114).

SUMMARY OF THE INVENTION

The present invention provides peptides or portions thereof, compositions, mimetics of these peptides or portions thereof or compositions, and pharmaceutical compositions comprising these peptides or portions thereof, compositions, or mimetics of these peptides or portions thereof or compositions, and methods for use of these peptides or portions thereof, compositions and pharmaceutical compositions which interact with SNCG and reduce SNCG-mediated resistance to treatment with anticancer drugs and/or inhibit SNCG-mediated tumorigenesis and/or cancer cell proliferation.

An aspect of the present invention relates to a peptide comprising at least one ankyrin repeat-like motif or a portion thereof or mimetic thereof which interacts with SNCG and reduces SNCG-mediated resistance to treatment with anti-cancer drugs and/or inhibits SNCG-mediated tumorigenesis and/or cancer cell proliferation. A peptide of the present invention comprises one or more of the following conserved amino acid residues from the consensus sequence of a single ankyrin repeat: a threonine at position 4; a proline at position 5; a leucine at position 6; a histidine at position 7; a glycine at positions 13 or 25; and/or a nonpolar residue at position 6, 8, 9, 10, 17, 18, 20, 21 and/or 22. More preferably, a peptide of the present invention comprises one or more of the following conserved amino acid residues: a glycine at position 2, 13 and/or 25; a threonine at position 4; a proline at position 5; a leucine at position 6 and/or 21; a histidine at position 7 and/or 14; and/or an alanine at position 9 and/or 26. More preferably, the peptide comprises at least one ankyrin repeat-like motif with the sequence $GX_1X_2X_3LHX_4AX_5X_6X_7$ $GHX_8X_9X_{10}X_{11}X_{12}X_{13}LX_{14}X_{15}X_{16}GA$ (SEQ ID NO: 7) or $GX_1X_2X_3LHX_4AX_5X_6X_7$ $GHX_8X_9X_{10}X_{11}X_{12}X_{13}LX_{14}X_{15}X_{16}GAX_{17}X_{18}NX_{19}X_{20}X_{21}X_{22}$ (SEQ ID NO:32), where $X_1$ is B1 or N; $X_2$ is B2; $X_3$ is B1; $X_4$ is B1 or Q; $X_5$ is B1 or B2; $X_6$ is B2 or K; $X_7$ is B2 or V; $X_8$ is B1 or K; $X_9$ is B3 or B4; $X_{10}$ is I or C; $X_{11}$ is B1; $X_{12}$ is B1, B2 or R; $X_{13}$ is B1 or B4; $X_{14}$ is B1 or T; $X_{15}$ is B2, B3 or R; $X_{16}$ is B1, B2 or E; $X_{17}$ is B1, B2 or E; $X_{18}$ is B1, B2 or D; $X_{19}$ is B1 or B2; $X_{20}$ is B1 or B3; $X_{21}$ is B1 or B2; $X_{22}$ is B1, B2 or E; B1 is G, A, V, L, I, M, F, W, or P; B2 is S, T, C, Y, N, or Q; B3 is D or E; and B4 is K, R or H; or a portion thereof. More preferred is ANK peptide KGNSALHVASQHGHLGCIQTLVRYGANVTMQNHG (SEQ ID NO:1) or a portion or mimetic thereof.

Another aspect of the present invention relates to compositions with a formula of Y-Z or Q-Y-Z, wherein Y comprises at least one ankyrin repeat-like motif peptide or portion thereof or mimetic thereof of the present invention which interacts with SNCG and reduces SNCG-mediated resistance to treatment with anticancer drugs and/or inhibits SNCG-mediated tumorigenesis and/or cancer cell proliferation; Z comprises a compound linked to Y that enhances the performance of Y; and in embodiments comprising Q, Q comprises another compound linked to Y-Z which also enhances performance of the Q-Y-Z composition. Q may be identical to Z or different from Z. Exemplary Z or Q compounds include, but are not limited to a targeting agent, a second agent for treatment of cancer, an agent which enhances solubility, absorption, distribution, half-life, bioavailability, stability, activity and/or efficacy, or an agent which reduces toxicity or side effects of the composition.

Another aspect of the present invention relates to pharmaceutical compositions comprising a peptide or portion thereof, a Y-Z or Q-Y-Z composition, or a mimetic of these which interacts with SNCG and reduces SNCG-mediated resistance to treatment with anticancer drugs thereby potentiating efficacy of an anticancer drug and/or inhibits SNCG-mediated tumorigenesis and/or cancer cell proliferation. The peptide or Y-Z or Q-Y-Z composition comprises at least one ankyrin repeat-like motif or a portion thereof or mimetic thereof. Preferably, the peptide or Y-Z or Q-Y-Z composition comprises a peptide having one or more of the following conserved amino acid residues from the consensus sequence of a single ankyrin repeat: a threonine at position 4; a proline at position 5; a leucine at position 6; a histidine at position 7; a glycine at positions 13 or 25; and/or a nonpolar residue at position 6, 8, 9, 10, 17, 18, 20, 21 and/or 22. More preferably, the peptide or Y-Z or Q-Y-Z composition comprises a peptide with one or more of the following conserved amino acid residues: a glycine at position 2, 13 and/or 25; a threonine at position 4; a proline at position 5; a leucine at position 6 and/or 21; a histidine at position 7 and/or 14; and/or an alanine at position 9 and/or 26. More preferably, the peptide or Y-Z or Q-Y-Z composition comprises a peptide with at least one ankyrin repeat-like motif of the sequence $GX_1X_2X_3LHX_4AX_5X_6X_7$ $GHX_8X_9X_{10}X_{11}X_{12}X_{13}LX_{14}X_{15}X_{16}GA$ (SEQ ID NO: 7) or $GX_1X_2X_3LHX_4$ $AX_5$ $X_6X_7$ $GHX_8X_9X_{10}X_{11}X_{12}X_{13}LX_{14}X_{15}X_{16}GAX_{17}X_{18}NX_{19}X_{20}X_{21}X_{22}$ (SEQ ID NO:32), where $X_1$ is B1 or N; $X_2$ is B2; $X_3$ is B1; $X_4$ is B1 or Q; $X_5$ is B1 or B2; $X_6$ is B2 or K; $X_7$ is B2 or V; $X_8$ is B1 or K; $X_9$ is B3 or B4; $X_{10}$ is I or C; $X_{11}$ is B1; $X_{12}$ is B1, B2 or R; $X_{13}$ is B1 or B4; $X_{14}$ is B1 or T; $X_{15}$ is B2, B3 or R; $X_{16}$ is B1, B2 or E; $X_{17}$ is B1, B2 or E; $X_{18}$ is B1, B2 or D; $X_{19}$ is B1 or B2; $X_{20}$ is B1 or B3; $X_{21}$ is B1 or B2; $X_{22}$ is B1, B2 or E; B1 is G, A, V, L, I, M, F, W, or P; B2 is S, T, C, Y, N, or Q; B3 is D or E; and B4 is K, R or H; or a portion thereof. More preferred is that the peptide or Y-Z or Q-Y-Z composition comprises ANK peptide KGNSALHVASQH-GHLGCIQTLVRYGANVTMQNHG (SEQ ID NO:1) or a portion or mimetic thereof.

Pharmaceutical compositions of the present invention may further comprise an anticancer drug. Preferably the anticancer drug is a microtubule inhibitor or a hormonal cancer therapy.

Another aspect of the present invention relates to a method for inhibiting SNCG-mediated tumorigenesis and/or cancer cell proliferation comprising administering to the cancer cells a peptide or portion thereof, a Y-Z or Q-Y-Z composition, or a mimetic of these which interacts with SNCG and reduces SNCG-mediated resistance to treatment with anticancer drugs and inhibits SNCG-mediated tumorigenesis and/or cancer cell proliferation. The peptide or Y-Z or Q-Y-Z composition administered comprises at least one ankyrin repeat-like motif or a portion thereof or mimetic thereof. Preferably, the peptide or Y-Z or Q-Y-Z composition comprises a peptide having one or more of the following conserved amino acid residues from the consensus sequence of a single ankyrin repeat: a threonine at position 4; a proline at position 5; a leucine at position 6; a histidine at position 7; a glycine at positions 13 or 25; and/or a nonpolar residue at position 6, 8, 9, 10, 17, 18, 20, 21 and/or 22. More preferably, the peptide or Y-Z or Q-Y-Z composition comprises a peptide with one or more of the following conserved amino acid residues: a glycine at position 2, 13 and/or 25; a threonine at position 4; a proline at position 5; a leucine at position 6 and/or 21; a histidine at position 7 and/or 14; and/or an alanine at position 9 and/or 26. More preferably, the peptide or Y-Z or Q-Y-Z composition comprises a peptide with at least one ankyrin repeat-like motif of the sequence $GX_1X_2X_3LHX_4AX_5X_6X_7GHX_8X_9X_{10}X_{11}X_{12}X_{13}LX_{14}X_{15}X_{16}GA$ (SEQ ID NO: 7) or $GX_1X_2X_3LHX_4AX_5X_6X_7GHX_8X_9X_{10}X_{11}X_{12}X_{13}LX_{14}X_{15}X_{16}GAX_{17}X_{18}NX_{19}X_{20}X_{21}X_{22}$ (SEQ ID NO:32), where $X_1$ is B1 or N; $X_2$ is B2; $X_3$ is B1; $X_4$ is B1 or Q; $X_5$ is B1 or B2; $X_6$ is B2 or K; $X_7$ is B2 or V; $X_8$ is B1 or K; $X_9$ is B3 or B4; $X_{10}$ is I or C; $X_{11}$ is B1; $X_{12}$ is B1, B2 or R; $X_{13}$ is B1 or B4; $X_{14}$ is B1 or T; $X_{15}$ is B2, B3 or R; $X_{16}$ is B1, B2 or E; $X_{17}$ is B1, B2 or E; $X_{18}$ is B1, B2 or D; $X_{19}$ is B1 or B2; $X_{20}$ is B1 or B3; $X_{21}$ is B1 or B2; $X_{22}$ is B1, B2 or E; B1 is G, A, V, L, I, M, F, W, or P; B2 is S, T, C, Y, N, or Q; B3 is D or E; and B4 is K, R or H; or a portion thereof. More preferred is that the peptide or Y-Z or Q-Y-Z composition comprises ANK peptide KGNSALHVASQHGHLGCIQTLVRYGANVTMQNHG (SEQ ID NO:1) or a portion or mimetic thereof.

Another aspect of the present invention relates to a method for potentiating activity of an anticancer drug against cancer cells comprising administering to the cancer cells a peptide or portion thereof, a Y-Z or Q-Y-Z composition, or a mimetic of these which interacts with SNCG and reduces SNCG-mediated resistance to treatment with anticancer drugs and an anticancer drug. The peptide or Y-Z or Q-Y-Z composition administered comprises at least one ankyrin repeat-like motif or a portion thereof or mimetic thereof. Preferably, the peptide or Y-Z or Q-Y-Z composition comprises a peptide having one or more of the following conserved amino acid residues from the consensus sequence of a single ankyrin repeat: a threonine at position 4; a proline at position 5; a leucine at position 6; a histidine at position 7; a glycine at positions 13 or 25; and/or a nonpolar residue at position 6, 8, 9, 10, 17, 18, 20, 21 and/or 22. More preferably, the peptide or Y-Z or Q-Y-Z composition comprises a peptide with one or more of the following conserved amino acid residues: a glycine at position 2, 13 and/or 25; a threonine at position 4; a proline at position 5; a leucine at position 6 and/or 21; a histidine at position 7 and/or 14; and/or an alanine at position 9 and/or 26. More preferably, the peptide or Y-Z or Q-Y-Z composition comprises a peptide with at least one ankyrin repeat-like motif of the sequence $GX_1X_2X_3LHX_4AX_5X_6X_7GHX_8X_9X_{10}X_{11}X_{12}X_{13}LX_{14}X_{15}X_{16}GA$ (SEQ ID NO:7) or $GX_1X_2X_3LHX_4AX_5X_6X_7GHX_8X_9X_{10}X_{11}X_{12}X_{13}LX_{14}X_{15}X_{16}GAX_{17}X_{18}NX_{19}X_{20}X_{21}X_{22}$ (SEQ ID NO:32), where $X_1$ is B1 or N; $X_2$ is B2; $X_3$ is B1; $X_4$ is B1 or Q; $X_5$ is B1 or B2; $X_6$ is B2 or K; $X_7$ is B2 or V; $X_8$ is B1 or K; $X_9$ is B3 or B4; $X_{10}$ is I or C; $X_{11}$ is B1; $X_{12}$ is B1, B2 or R; $X_{13}$ is B1 or B4; $X_{14}$ is B1 or T; $X_{15}$ is B2, B3 or R; $X_{16}$ is B1, B2 or E; $X_{17}$ is B1, B2 or E; $X_{18}$ is B1, B2 or D; $X_{19}$ is B1 or B2; $X_{20}$ is B1 or B3; $X_{21}$ is B5 or B2; $X_{22}$ is B1, B2 or E; B1 is G, A, V, L, I, M, F, W, or P; B2 is S, T, C, Y, N, or Q; B3 is D or E; and B4 is K, R or H; or a portion thereof. More preferred is that the peptide or Y-Z or Q-Y-Z composition comprises ANK peptide KGNSALHVASQHGHLGCIQTLVRYGANVTMQNHG (SEQ ID NO:1) or a portion or mimetic thereof. In this method, the peptide or portion thereof, a Y-Z or Q-Y-Z composition, or a mimetic of these which interacts with SNCG and reduces SNCG-mediated resistance to treatment with anticancer drugs and the anticancer drug may be administered to the cancer cells simultaneously as a single pharmaceutical composition, at the same time in separate pharmaceutical compositions or at different times. Preferred anticancer drugs used in this method are microtubule inhibitors and hormonal cancer treatments.

Yet another aspect of the present invention relates to a method for treating cancer in a patient comprising administering to the patient a peptide or portion thereof, a Y-Z or Q-Y-Z composition, or a mimetic of these which interacts with SNCG and reduces SNCG-mediated resistance to treatment with anticancer drugs and an anticancer drug. The peptide or Y-Z or Q-Y-Z composition administered comprises at least one ankyrin repeat-like motif or a portion thereof or mimetic thereof. Preferably, the peptide or Y-Z or Q-Y-Z composition comprises a peptide having one or more of the following conserved amino acid residues from the consensus sequence of a single ankyrin repeat: a threonine at position 4; a proline at position 5; a leucine at position 6; a histidine at position 7; a glycine at positions 13 or 25; and/or a nonpolar residue at position 6, 8, 9, 10, 17, 18, 20, 21 and/or 22. More preferably, the peptide or Y-Z or Q-Y-Z composition comprises a peptide with one or more of the following conserved amino acid residues: a glycine at position 2, 13 and/or 25; a threonine at position 4; a proline at position 5; a leucine at position 6 and/or 21; a histidine at position 7 and/or 14; and/or an alanine at position 9 and/or 26. More preferably, the peptide or Y-Z or Q-Y-Z composition comprises a peptide with at least one ankyrin repeat-like motif of the sequence $GX_1X_2X_3LHX_4AX_5X_6X_7GHX_8X_9X_{10}X_{11}X_{12}X_{13}LX_{14}X_{15}X_{16}GA$ (SEQ ID NO: 7) or $GX_1X_2X_3LHX_4AX_5X_6X_7GHX_8X_9X_{10}X_{11}X_{12}X_{13}LX_{14}X_{15}X_{16}GAX_{17}X_{18}NX_{19}X_{20}X_{21}X_{22}$ (SEQ ID NO:32), where $X_1$ is B1 or N; $X_2$ is B2; $X_3$ is B1; $X_4$ is B1 or Q; $X_5$ is B1 or B2; $X_6$ is B2 or K; $X_7$ is B2 or V; $X_8$ is B1 or K; $X_9$ is B3 or B4; $X_{10}$ is I or C; $X_{11}$ is B1; $X_{12}$ is B1, B2 or R; $X_{13}$ is B1 or B4; $X_{14}$ is B1 or T; $X_{15}$ is B2, B3 or R; $X_{16}$ is B1, B2 or E; $X_{17}$ is B1, B2 or E; $X_{18}$ is B1, B2 or D; $X_{19}$ is B1 or B2; $X_{20}$ is B1 or B3; $X_{21}$ is B1 or B2; $X_{22}$ is B1, B2 or E; B1 is G, A, V, L, I, M, F, W, or P; B2 is S, T, C, Y, N, or Q; B3 is D or E; and B4 is K, R or H; or a portion thereof. More preferred is that the peptide or Y-Z or Q-Y-Z composition comprises ANK peptide KGNSALHVASQHGHLGCIQTLVRYGANVTMQNHG (SEQ ID NO:1) or a portion or mimetic thereof. In this method the peptide or portion thereof, the Y-Z or Q-Y-Z composition, or the mimetic of these which interacts with SNCG and reduces SNCG-mediated resistance to treatment with anticancer drugs and the anticancer drug may be administered to the patient simultaneously as a single pharmaceutical composition, at the same time in separate pharmaceutical compositions or at different times. Preferred anticancer drugs used in this method are microtubule inhibitors and hormonal anticancer therapies.

BRIEF DESCRIPTION OF THE FIGURES

FIG. 2A provides fluorescence emission spectra of SNCG (30 µM) at an excitation wavelength of 274 nm using varying concentrations of ANK peptide as ligand. Ligand concentrations: 0, 10, 20, 30, 40, 50, 92, 133, 171, 206, and 240 µM are represented by B-L respectively. The measurements were carried out in 10 mM sodium phosphate buffer, pH 7.0, at 25° C. FIG. 2B provides phase diagrams (parametric $I_{310}$ vs. $I_{370}$ dependences) of the ANK peptide KGNSALHVASQHGHLGCIQTLVRYGANVTMQNHG (SEQ ID NO:1) binding to SNCG. Numbers I, II and III correspond to three linear stages. FIG. 2C provides a fluorescence emission spectra of SNCG (30 µM) and ANK peptide (SEQ ID NO:1; 240 µM) in the presence of 0.02 mg/mL 1-anilino-8-naphthalene sulphonate (ANS). All samples were in 10 mM sodium phosphate buffer, pH 7.0, and measurements were carried out at 25° C.

FIG. 3A shows replicates of the interaction between ANK peptide and glutathione S-transferase (GST)-SNCG with GST-SNCG at concentrations of 4.413 µM (1), 2.648 µM (2) and 0.662 µM (3). FIG. 3B shows the ITC analysis of the binding of ANK peptide to the GST-SNCG in vitro. The upper panel shows the raw heat change elicited by successive injections of ANK peptide into a solution of GST-SNCG, whereas the bottom panel depicts the normalized integration data (kcal/mol of peptide as a function of the molar ratio of peptide to the GST-SNCG), as well as the fitting to the sequential binding site model.

FIG. 4A(a) is a photograph of uninjected MCF7-Neo cells; FIG. 4A(b) is a photograph of uninjected MCF7-SNCG cells; FIG. 4A(c-d) are photographs from replicate experiments where MCF7-SNCG cells were microinjected with ANK peptide and treated with 0.5 µM of nocodazole; FIG. 4A(e) is a photograph of MCF7-Neo cells microinjected with ANK peptide without nocodazole treatment; FIG. 4A(f) is a photograph of uninjected MCF7-SNCG cells treated with 0.5 µM of nocodazole; FIG. 4A (g-h) are photographs from replicate experiments where MCF7-Neo cells were microinjected with ANK peptide and treated with 0.5 µM of nocodazole.

FIG. 5A is a western blot depicting detection of EGFP-ANK expression in COS7 cells. Lanes 2 and 3 were samples transfected with different clones, cl-4 and cl-8, respectively, of pEGFP-ANK plasmid. In FIG. 5B, MCF7-SNCG cells were transfected with pEGFP-ANK, fixed on a cover slip, permeabilized and probed with anti-SNCG and anti-GFP antibodies to observe co-localization. Fluorescent cells were visualized using an ×100 objective (oil) on an inverted confocal microscope (Leica). FIGS. 5C and 5D are western blots showing association of SNCG and ANK peptide as evidenced by co-IP of SNCG with EGFP-ANK in MCF7-SNCG and MCF7-neo cells. In these experiments, MCF7-SNCG and MCF7-neo cells were transfected with pEGFP-ANK or pEGFP plasmids. Two days after transfection, total cell lysates were harvested, and 2 mg of total cell lysate per sample was used to perform co-IP with anti-SNCG antibody (SC-10698; FIG. 5C) or GST pull down using GST-SNCG overexpressed in E. coli (FIG. 5D). GST served as a control. The samples were separated by SDS-PAGE, and the membrane was sequentially probed with anti-GFP and anti-SNCG antibodies for co-IP and with anti-GFP, anti-GST and anti-SNCG antibodies for the GST pull down experiments.

FIG. 6 shows the disruption of the BubR1-SNCG association in the presence of ANK peptide KGNSALHVASQHGHLGCIQTLVRYGANVTMQNHG (SEQ ID NO:1). In this western blot, co-IP of SNCG and BubR1 in the presence and absence of EGFP-ANK is shown. COS7 cells were transfected with pCS2-BubR1, pCI-SNCG, pEGFP-ANK or the control vector pEGFP at equal molar ratios. Co-immunoprecipitation was conducted using anti-SNCG antibody as described in Example 8. The left panel of the western blot shows the presence of myc-BubR1 in the IP complex in the absence of ANK peptide but not in the presence of ANK peptide. The right panel shows similar expression levels of BubR1, ANK and SNCG proteins on western blots using total cell lysates.

FIG. 7C shows results from flow cytometry performed to measure apoptotic and mitotically arrested cells after treatment with paclitaxel in the presence and absence of ANK. MCF7-SNCG cells transfected with pEGFP-ANK were treated with 0.5 µM paclitaxel for 18 hours. Left panels represent cell cycle analysis of ANK positive and negative cells to measure apoptosis only. PI staining clearly demonstrates higher cell killing in the presence of the ANK peptide (upper left). Right panels are a representative scattergram for mitotic arrest measurement using anti-phospho-H3 primary antibody and Allophycocyanin (APC) goat anti-rabbit secondary antibody staining for ANK positive and negative cells. FIG. 7D is a bar graph showing the statistics of the apoptotic cells and mitotic arrest cells. The two bars on the left represent PI staining and the remaining two bars on the right show anti-phospho-H3 staining. The data shown is representative of 3 separate experiments ($p<0.01$).

DETAILED DESCRIPTION OF THE INVENTION

Figure 1:
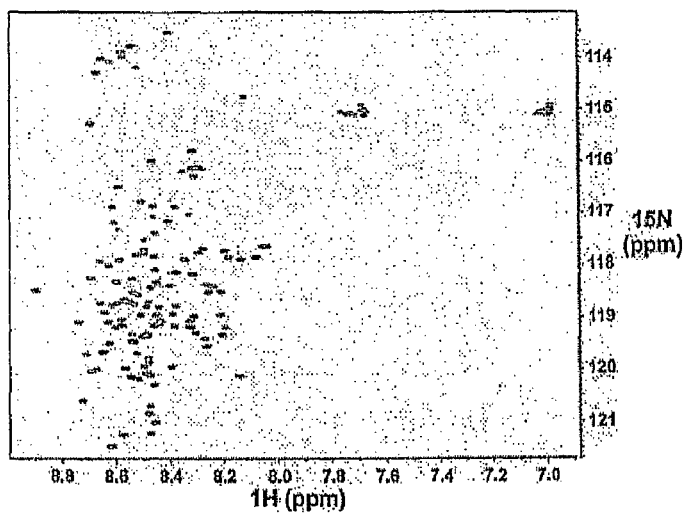
FIG. 1A provides a $^1H$-$^{15}N$ HSQC spectrum of intrinsically disordered SNCG and its interaction with ANK peptide KGNSALHVASQHGHLGCIQTLVRYGANVTMQNHG (SEQ ID NO:1). The measurement was carried out using 0.35 mM $^{15}N$-labeled SNCG in 10 mM sodium phosphate, pH 7.0 at 5° C.
FIGS. 1B and 1C provide far-UV circular dichroism (CD) spectra of SNCG (10 µM) with titration of ANK peptide KGNSALHVASQHGHLGCIQTLVRYGANVTMQNHG (SEQ ID NO:1) at concentrations of 2 µM, 12 µM and 24 µM (FIG. 1B) and 25 µM, 50 µM and 100 µM (FIG. 1C). Measurements were carried out in 10 mM sodium phosphate buffer, pH 7.0, at 25° C., in a cell of path length 0.1 mm using an OLIS RSM spectrometer. Spectra patterns correspond to random coil structures.
Figure 1:
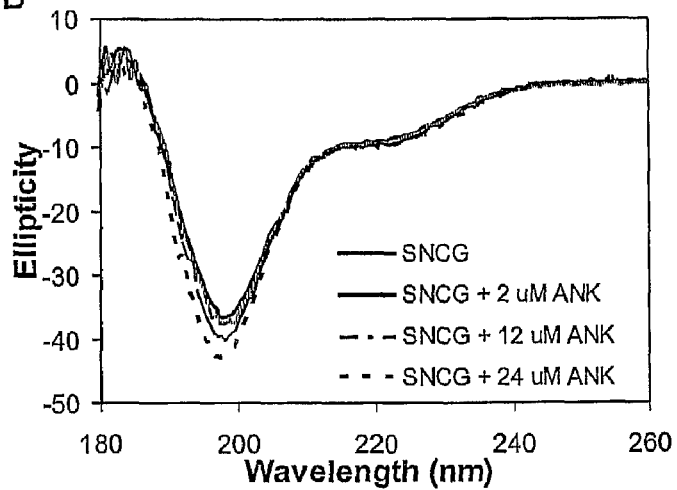
Figure 1:
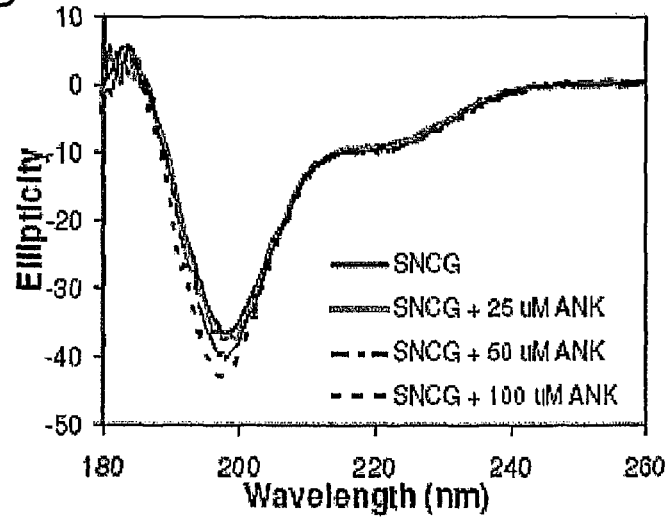

The oncogenic protein synuclein-gamma (SNCG) belongs to a family of intrinsically disordered proteins that have a wide range of significance in living systems. However, their structural and functional characteristics are still poorly understood (Uversky, V. N. Protein Sci. 2002 11:739-756; Tompa, P. Trends Biochem. Sci. 2002 27:527-533; Uversky et al. J. Mol. Recognit. 2005 18:343-384; Uversky, V. N. Eur. J. Biochem. 2002 269:2-12; Romero et al. Appl. Bioinformatics 2004 3:105-113; Iakoucheva et al. J. Mol. Biol. 2002 323:573-584). Other members of this neuronal protein synuclein family include synuclein-α (SNCA) and synuclein-β (SNCB) (Clayton, D. F. and George, J. M. Trends Neurosci. 1998 21:249-254). The exogenous expression of synuclein-gamma (SNCG) in breast cancer cells has been linked to stimulated proliferation, increased cell invasion and metastasis, and resistance to anticancer drugs, particularly anti-microtubule chemotherapy (Liu et al. Breast Cancer Res. Treat. 2000 62:99-107; Lu et al. J. Biol. Chem. 2002 277:31364-31372; Jiang et al. Cancer Res. 2004 64:4539-4546; Inaba et al. Breast Cancer Res. Treat. 2005 94:25-35; Gupta et al. Oncogene 2002 22:7593-7599). SNCG mRNA and protein are not expressed in normal breast tissue or tissues with benign breast diseases but are abundantly expressed in a high percentage of invasive and metastatic breast carcinomas (Ji et al. Cancer Res. 1997 57:759-764; Bruening et al. Cancer 2000 88:2154-2163; Wu et al. Cancer Epidemiol. Biomarkers Prev. 2003 12:920-925). A recent report of the prominent expression of SNCG in 8 different types of human cancers, including liver, esophageal, colon, gastric, lung, prostate, cervical and breast cancer (Liu et al. Cancer Res. 2005 65:7635-7643) is indicative of SNCG expression status having a broad effect in cancer metastasis and patient responses to anticancer drugs in many types of cancer.

One of the molecular mechanisms underlying the oncogenic functions of SNCG is its interaction with BubR1 and the consequential inhibition of BubR1-mediated mitotic checkpoint functions (Inaba et al. Breast Cancer Res. Treat. 2005 94:25-35; Gupta et al. Oncogene 2002 22:7593-7599). Additional evidence shows that the interaction of BubR1 with CENP-E, which is critically required for mitotic checkpoint signaling, is impaired in the presence of SNCG, thereby suggesting that SNCG may inhibit BubR1 function by interfering with the BubR1 CENP-E interaction (Inaba et al. Breast Cancer Res. Treat. 2005 94:25-35).

SNCG is also a chaperone protein in the (Hsp)-based multiprotein chaperone complex for stimulation of ligand-dependent estrogen receptor (ER)-α signaling and stimulates hormone-responsive tumorigenesis (Jiang et al. Cancer Research 2004 64:4539-4546).

The inventors have now identified a synthetic peptide based on a single ankyrin repeat-like motif which associates with SNCG and interferes with the SNCG-BubR1 interaction. The peptide overrides the inhibitory effects of elevated SNCG on anti-microtubule drugs and results in restored anti-microtubule drug mediated mitotic arrest. Given the ability of this peptide to associate with SNCG, it is reasonable to expect that the peptide can also inhibit SNCG stimulation of ER-α signaling and hormone responsive tumorigenesis as well as drug resistance to estrogen receptor modulators such as tamoxifen.

To the best of the inventors' knowledge, this is the first disclosure of a single ankyrin repeat-like motif interacting with any protein and/or producing a biological effect and/or leading to a phenotypic change in a cell. In this synthetic peptide KGNSALHVASQHGHLGCIQTLVRYGAN-VTMQNHG (SEQ ID NO:1), referred to herein as the ANK peptide, nine conserved ankyrin repeat residues (Gly-2, Leu-6, His-7, Ala-9, Gly-13, His-14, Leu-21, Gly-25, and Ala-26) are included.

The interaction of SNCG with the ANK peptide was examined by various biophysical and cell biological approaches.

Experiments were first performed to confirm the previous observation (Uversky, V. N. Protein Sci. 2002 11:739-756) that SNCG is intrinsically disordered. The $^1$H-$^{15}$N HSQC spectrum of native SNCG was characterized by narrow linewidths and limited $^1$H chemical shift dispersion (FIG. 1A). This is indicative of conformational averaging within a rapidly interconverting ensemble and demonstrates that SNCG is intrinsically disordered. The far-UV CD spectrum of SNCG was characteristic of an intrinsically disordered polypeptide chain as well, as evidenced by the absence of bands in the 210-230 nm region and an intensive minima at approximately 196 nm (See FIGS. 1B and 1C). Upon interaction, far UV CD showed that SNCG undergoes no significant conformational changes and remains disordered. This contrasts to the coupled binding and folding that has often been observed for intrinsically disordered proteins (Dyson, H. J and Wright, P. E. Curr. Opin. Struct. Biol. 2002 12:54-60). The SNCG-ANK interaction is similar to the calmodulin-binding fragment of caldesmon (CaD136), which binds a single calmodulin molecule with relatively high affinity while undergoing only very moderate folding (Permyakov et al. Proteins 2003 53:855-862). These calmodulin studies and our SNCG findings represent a newly recognized class of intrinsically disordered proteins that are able to bind their ligands while remaining disordered and affirm the biological relevance of intrinsic disorder.

Titration of SNCG with the ANK peptide also gave rise to far-UV spectra characteristic of an unfolded protein (FIG. 1B) and produced no significant changes in calculated secondary structure. See Table 1 below.

TABLE 1

| Structure (%) | SNCG | SNCG + 2.0 µM ANK Peptide | SNCG + 12 µM ANK Peptide | SNCG + 24 µM ANK Peptide |
| --- | --- | --- | --- | --- |
| Helix | 28.7 | 29.2 | 30.0 | 30.4 |
| Antiparallel | 9.10 | 9.00 | 8.80 | 8.70 |
| Parallel | 10.5 | 10.3 | 10.0 | 9.90 |
| Beta-Turn | 17.7 | 17.6 | 17.4 | 17.3 |
| Random Coil | 36.4 | 36.0 | 35.4 | 35.0 |

Intrinsic tyrosine fluorescence provides a convenient means of monitoring the binding between the ANK peptide and SNCG. Neither SNCG nor the ANK peptide has a tryptophan residue. However, both have a single tyrosine, and there are two phenylalanine residues in SNCG. Thus, the intrinsic fluorescence of this system is expected to have a maximal intensity at 305 nm. However, the intrinsic tyrosine fluorescence of SNCG was found to be maximal at 345 nm. A comparable position of maximal fluorescence has been observed for several other proteins containing tyrosine but lacking tryptophan, e.g., adrenodoxin (Lim, B. T. and Kimura, T. J. Biol. Chem. 1980 255:2440-2444). This fluorescence maximum coincides with the tyrosinate emission peak. Although it is unlikely that at pH 7 there is any tyrosinate present in the ground state, the origin of this anomalous tyrosine emission has been assigned to an intramolecular excited state proton transfer from phenolic hydroxyl to a proton acceptor (Szabo et al. FEBS Lett. 1978 94:249-252). Alternatively, an intramolecular interaction between the phenolic hydroxyl group of the tyrosine residue and a carboxyl group of aspartic or glutamic acid residues may occur, causing the tyrosine to possess an anomalous pKa. It is also possible that long-range interactions may take place between phenylalanine and tyrosine residues thus affecting tyrosine fluorescence (Lim, B. T. and Kimura, T. J. Biol. Chem. 1980 255:2440-2444). Importantly, it has been documented that the treatment of the adrenodoxin with guanidine HCl, urea, LiCl, high temperature or low pH resulted in the normalization of tyrosine fluorescence with the fluorescence emission peak at 305 nm (Lim, B. T. and Kimura, T. J. Biol. Chem. 1980 255:2440-2444). Removal of these denaturing agents resulted in the restoration of the fluorescent anomaly. Based on these observations, it has been concluded that the conformation-determined microenvironment of the tyrosine residue might give rise to the anomalous tyrosine fluorescence (Lim, B. T. and Kimura, T. J. Biol. Chem. 1980 255:2440-2444).

It is therefore believed that the observed red-shifted intrinsic fluorescence of SNCG indicates that Tyr-39 is located in a unique microenvironment. This is an intriguing observation considering that SNCG is intrinsically disordered. Recently, it has been reported that another intrinsically disordered protein, CaD136, possesses some residual structure which was suggested to be responsible for the relatively asymmetric environment of tryptophan residues in this protein (Permyakov et al. Proteins 2003 53:855-862).

Addition of the ANK peptide resulted in a pronounced blue shift in $\lambda_{max}$ (See FIG. 2A). By plotting fluorescence changes versus concentration of ANK peptide, a dissociation constant ($K_d$) value of approximately 100 µM was estimated. To understand the molecular mechanism of the SNCG-ANK interaction, the method of parametric dependencies was applied (See FIG. 2B). It has been demonstrated that the dependence $I(\lambda_1)= f(I\lambda_2))$ is linear for the all-or-none transition between two different conformations, whereas the non-linearity of this function reflects the sequential character of structural transformations, with each linear portion describing the individual all-or-none transition. FIG. 2B shows that $I_{310}$ versus $T_{370}$ plot has at least three linear regions, suggesting a complex mechanism of ANK peptide binding to SNCG involving at least three distinct stages.

The pronounced blue shift in the emission spectra, reflecting the normalization of tyrosine fluorescence, upon addition of the ANK peptide, can be attributed to the distortion in the residual SNCG structure induced by ANK peptide binding. The lone tyrosine residue of SNCG is located near the N-terminus (Tyr-39), suggesting that the ANK binding site is either located in this region or a region that can directly impact the N-terminus. The C-terminal region of SNCG is believed to interact with BubR1 (Gupta et al. Oncogene 2003 22:7593-7599). Since this region is not conserved with SNCA, it is believed that ANK binding may occur at the N-terminal or central region of SNCG. While not being bound to any theory, it is possible that the C-terminal region is in close proximity to the N-terminal region despite the absence of regular folded structure, explaining the fluorescence results and the apparent disruption of the SNCG-BubR1 interaction. In SNCA, paramagnetic relaxation enhancement NMR experiments have shown that there are similar long-range residual tertiary contacts involving the charged C-terminal region and the middle section of the protein (Dedmon et al. J. Am. Chem. Soc. 2005 127:476-477; Ohshima et al. Cancer Lett. 2000 158:141-150). Results described herein are indicative of key functional segments in intrinsically disordered proteins having certain spatial relationships despite the lack of regular folded structure.

ANS fluorescence was also utilized to study the conformational properties of SNCG and the SNCG-ANK peptide interaction (See FIG. 2C). Changes in ANS fluorescence intensity are frequently used to monitor formation of partially folded intermediates during protein unfolding and refolding (Semisotnov et al. Biopolymers 1991 31:119-128), as well as to analyze the hydrophobic surfaces of proteins (Stryer, L. J. Mol. Biol. 1965 13:482-495). The interaction of ANS with solvent-exposed hydrophobic clusters is accompanied by a considerable increase in the dye fluorescence intensity and a pronounced blue shift of the fluorescence maximum. FIG. 2C shows that SNCG did not interact with ANS, confirming that this protein is intrinsically disordered and does not possess large solvent-exposed hydrophobic patches that are typical of folded conformations. The addition of ANK peptide induced significant changes in ANS fluorescence properties, including a dramatic increase in the fluorescence intensity and a blue shift in $\lambda_{max}$. This suggests that the ANK peptide can effectively interact with ANS. Importantly, formation of the SNCG-ANK complex is accompanied by an approximate 20% decrease in ANS fluorescence intensity of only peptide which is affected by the presence of SNCG, confirming the interaction between SNCG and ANK peptide.

Figure 3:
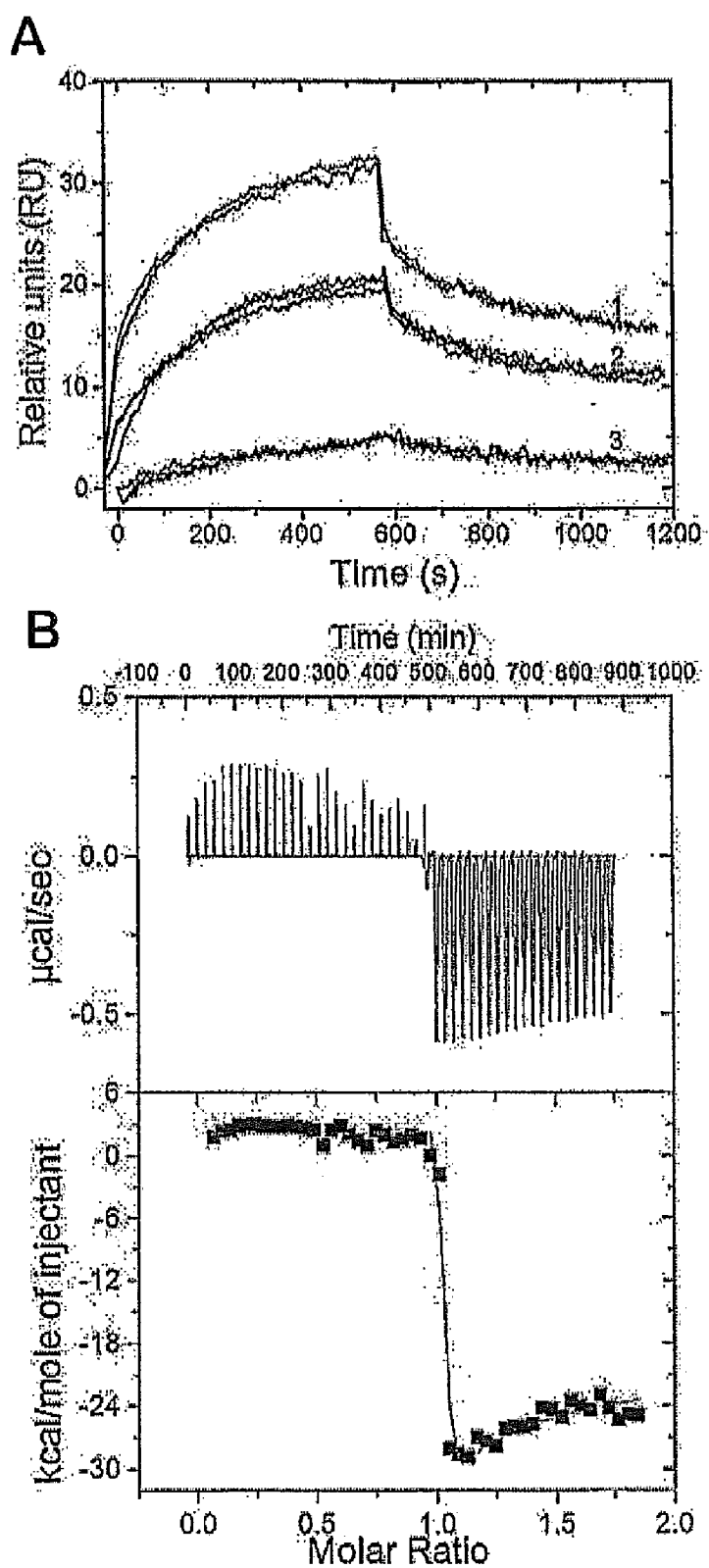
FIG. 3 shows the interaction between SNCG and ANK peptide KGNSALHVASQHGHLGCIQTLVRYGANVTMQNHG (SEQ ID NO:1) monitored by surface plasmon resonance (SPR) and isothermal titration calorimetry (ITC).

Kinetics of the SNCG-ANK interaction were determined. Using immobilized ANK peptide and a GST-SNCG analyte, surface plasmon resonance (SPR) demonstrated binding of SNCG to the ANK peptide. FIG. 3A shows sensograms measured at several GST-SNCG concentrations. Sensograms were deconvoluted globally, using a simultaneous fit for both association ($k_a$, $M^{-1}s^{-1}$) and dissociation ($k_d$, $s^{-1}$). Global fits were obtained for the two-phase reaction (conformation change) model with rate constants of $k_{a1}$ ($2.59 \times 10^{-3}$ $M^{-1}$ $s^{-1}$), $k_{d1}$ ($0.014$ $s^{-1}$), $K_{a2}$ ($3.32 \times 10^{-3}$ $M^{-1}$ $s^{-1}$), $k_{d2}$ ($8.02 \times 10^{-4}$ $s^{-1}$). Overall, the apparent $K_d$ was found to be 73.4 µM for the GST-SNCG-ANK peptide interaction. This data is in good accord with the values obtained from the fluorescence experiment where ANK peptide was titrated in SNCG. There was no significant decrease in analyte binding capacity to ANK for the duration of the experiments and the active ANK peptide surfaces were very stable. No binding was observed when GST was used as the analyte, thus confirming that SNCG was responsible for the observed interaction between GST-SNCG and ANK peptide.

Isothermal titration calorimetry was also used to thermodynamically characterize the SNCG-ANK interaction (See FIG. 3B). Because the thermodynamic properties of an interaction often reflect its structural characteristics, it was interesting to note an endothermic phase followed by an exothermic phase. The thermodynamics of the peptide titration in GST-SNCG solution exhibited excellent agreement with ideal binding (see FIG. 3B), indicating the presence of one high affinity and multiple low affinity sequential binding sites. The heat of dilution was measured by titrating ANK peptide in buffer alone. This was generally small and subtracted from each binding titration curve. A measured $K_d$=70±5 µM and ΔH=2.174±0.2 kcal/mol for the first binding site and in the several fold lower affinity range for other sequential binding sites were observed. These results were in very good agreement with SPR and fluorescence analysis, validating the observed interaction in solution as well as in the immobilized form.

Figure 4:
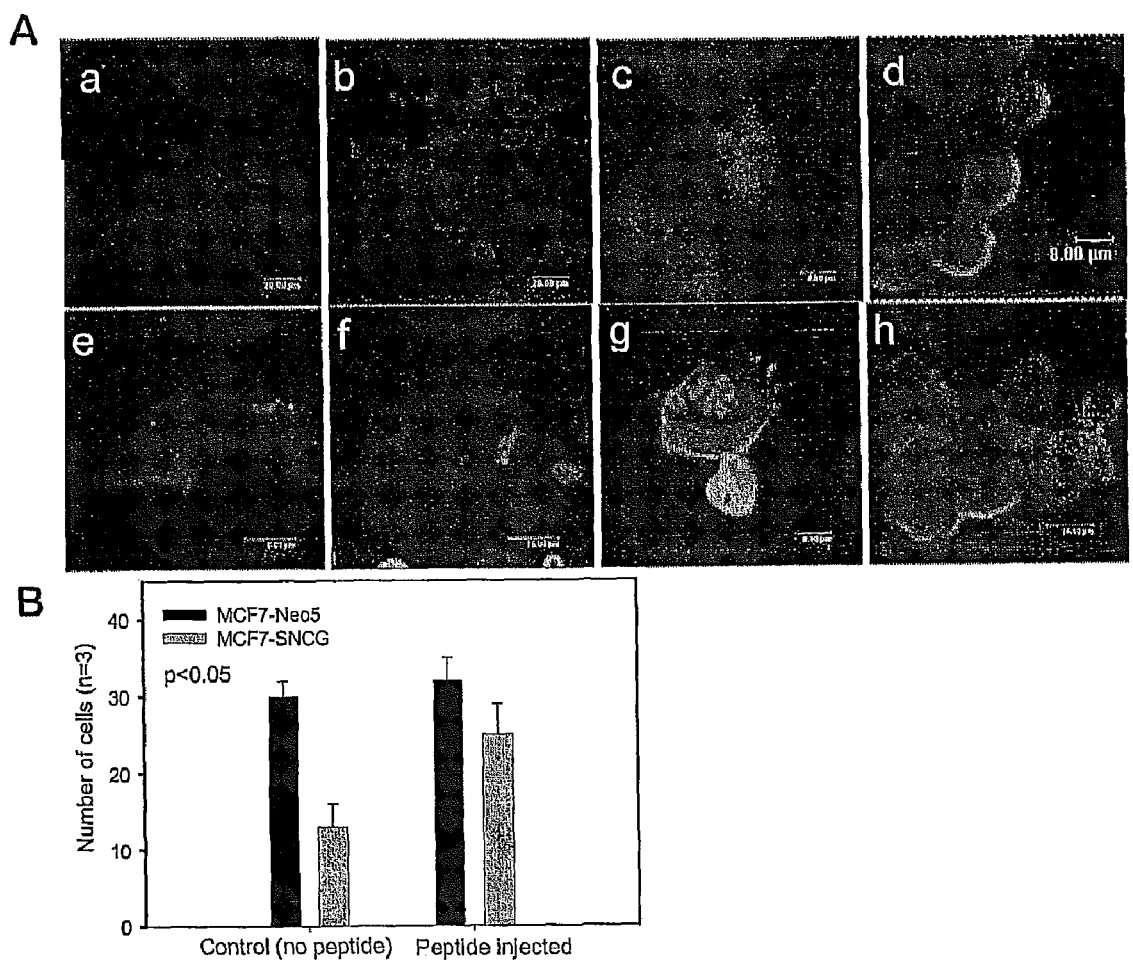
FIG. 4A (a through h) provides photographs of microinjection of ANK peptide KGNSALHVASQHGHLGCIQTLVRYGANVTMQNHG (SEQ ID NO:1) to observe interference with the SNCG-BubR1 interaction. Cells were fixed with paraformaldehyde as described in Example 6 and then visualized using DAPI. Microinjected cells were identified using goat IgG probed with donkey anti-goat IgG labeled with Alexa Fluor 488.
FIG. 4B is a bar graph that shows the statistics of the viability of MCF7-Neo5 cells versus MCF7-SNCG cells. The Y-axis shows the number of cells undergoing mitotic arrest/apoptosis. The left panel shows uninjected cells and the right panel shows ANK peptide injected cells, both treated with the anti-microtubule drug nocodazole. MCF7-Neo5 cells were not significantly affected by microinjection of ANK peptide (see black bars). MCF7-SNCG cells microinjected with ANK peptide exhibited a significant ($p<0.05$) increase in the number of cells in mitotic arrest and/or apoptosis (see grey bars).

ANK peptide interference with SNCG-BubR1 association in vivo was examined in a stable breast cancer cell line MCF7 expressing SNCG (MCF7-SNCG) and a control SNCG negative cell line (MCF7-Neo). Microinjection efficiency and viability were excellent when cells were injected with goat IgG as a control, demonstrating that background effects of microinjection and antibody were minimal in both cell lines. Significant numbers of cells survived after treatment with the ANK peptide by microinjection in both cell lines. After microinjection, cells were treated with 0.5 µM nocodazole for 24 hours and the fraction of mitotically arrested cells was counted. As shown in FIG. 4A, when the cells without ANK injection were treated with nocodazole, MCF7-Neo cells exhibited a significantly higher degree of mitotic arrest as compared to MCF7-SNCG cells. In contrast, injection of the ANK peptide into MCF7-SNCG cells significantly (p<0.05) increased the level of mitotically arrested cells to a level comparable to that in MCF7-Neo cells (See FIG. 4B, grey bars). These results are indicative of ANK peptide functioning as a SNCG inhibitor.

To further examine the utility of the ANK peptide as a therapeutic tool against SNCG-caused drug resistance, this peptide was expressed in breast cancer cells. ANK peptide nucleotide sequences were cloned into pEGFP-C2 vector (pEGFP-ANK), and ANK peptide was expressed as a fusion protein with its amino-terminal linked to EGFP protein. Plasmids pEGFP-ANK and pEGFP were separately transfected into cells. Western blotting using anti-GFP antibody showed specific signals of EGFP as a 33 kDa protein and EGFP-ANK as approximately a 37 kDa fusion protein (See FIG. 5A). The intracellular localization of EGFP-ANK was demonstrated by green fluorescent signals to be co-localized with SNCG in the cytoplasm.

MCF7-SNCG cells were also transfected with pEGFP-ANK, fixed on a cover slip permeabilized and probed with anti-SNCG and anti-GFP antibodies to observe co-localization. Fluorescent cells were visualized using an ×100 objective (oil) on an inverted confocal microscope (Leica). See FIG. 5B. Co-localization is indicative of both proteins existing in close proximity in the same cellular compartment and provides indirect evidence of protein-protein association.

Figure 5:
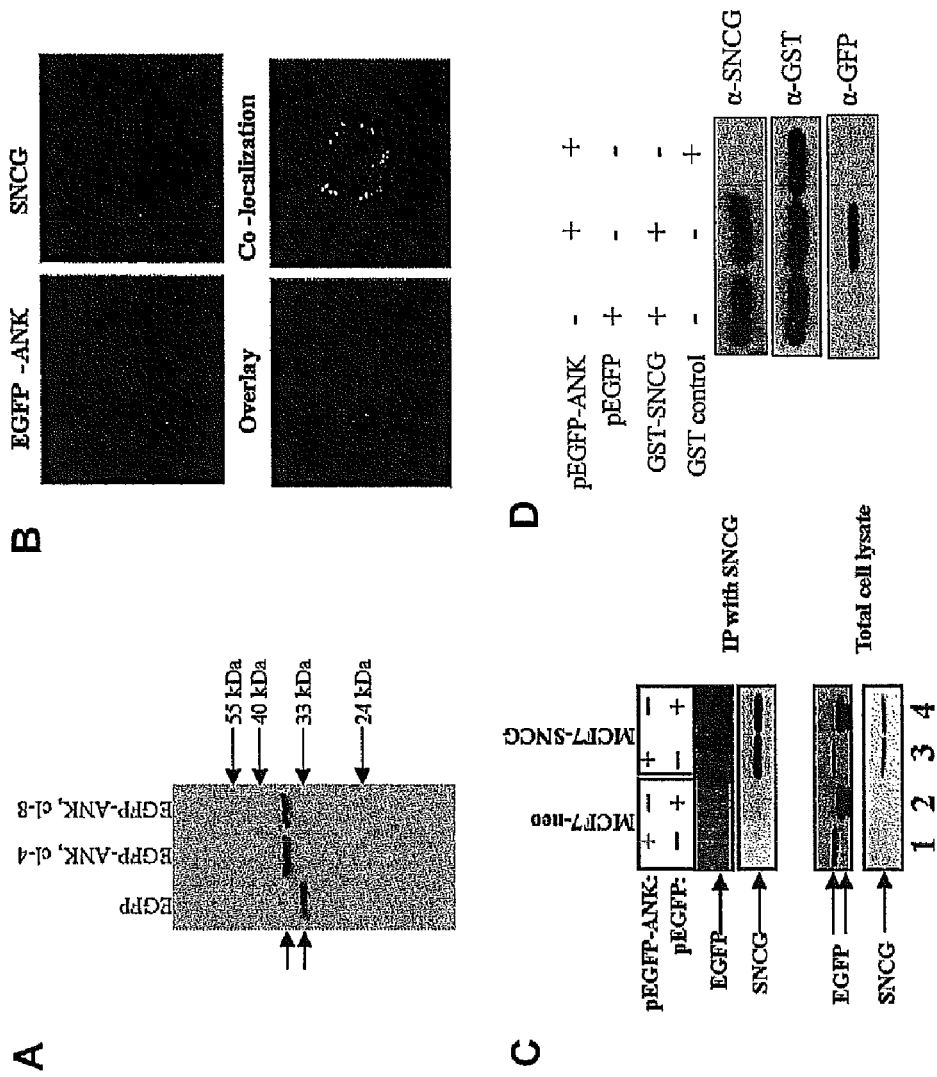
FIGS. 5A through 5D show co-localization, co-immunoprecipitation (co-IP) and GST pull down experiments, using an enhance green fluorescent protein (EGFP)-ANK fusion protein, which confirm that SNCG associates with the ANK peptide in vivo.

In vivo binding of ANK to SNCG was examined in co-immunoprecipitation (co-IP) experiments (See FIGS. 5C and 5D). MCF7-SNCG (lanes 3 & 4) cells were transfected with pEGFP-ANK (lane 3 of FIG. 5C) or the control vector pEGFP (lane 4 of FIG. 5C). In this experiment, MCF7-neo cells were included as negative controls (lanes 1 & 2). Two days after transfection, cell lysates were prepared and IP with anti-SNCG antibody was conducted. The presence of EGFP-ANK in SNCG IP complexes obtained from different transfected cells was detected by western blot using anti-GFP antibody. The membrane was subsequently reprobed with anti-SNCG antibody to demonstrate equal amounts of SNCG in IP complexes of MCF7-SNCG cell lysates. The upper panel in FIG. 5C shows that when anti-SNCG IP complexes were probed with GFP antibody, only EGFP-ANK but not EGFP alone is found to co-precipitate with SNCG (lane 3) in MCF7-SNCG cells. EGFP-ANK was also not in the IP complexes of neo cells. The lower panel shows the immunoblotting of anti-SNCG and anti-GFP in total cell lysates. Thus, FIG. 5D provides further evidence that SNCG is capable of immunoprecipitating EGFP-ANK.

Accordingly, the results of the co-IP experiments depicted in FIGS. 5C and 5D clearly demonstrate the direct intracellular binding of ANK peptide to SNCG.

BubR1 has been identified as a cellular target of SNCG through yeast two-hybrid and co-IP (Gupta et al. Oncogene 2003 22:2593-7599). The binding of SNCG to BubR1 is believed to result in compromised mitotic checkpoint function as demonstrated by increased resistance of cancer cells to anti-microtubule drugs. Experiments were performed to determine whether the binding of ANK to SNCG would directly affect SNCG interaction with BubR1. In these experiments COS7 cells were transfected with pCS2BubR1, pCI-SNCG, pEGFP-ANK or the control vector PEGFP at equal molar ratios. Two days post transfection, cells were harvested for IP with anti-SNCG antibody. The presence of the myc-tagged BubR1 in IP complexes was detected by western blot using anti-Myc antibody. The membrane was then sequentially probed with anti-GFP antibody and followed with anti-SNCG antibody. The left panel in FIG. 6 shows that when anti-SNCG IP complexes were probed with myc antibody, the myc-BubR1 was found to co-precipitate with SNCG in the absence of EGFPANK and myc-BubR1 signal was not detected in the IP complex of cells expressing the ANK peptide. In contrast, anti-GFP antibody only detected the GFP signal in the IP complex obtained from cells expressing EGFP-ANK and not from cells expressing GFP only. The right panel of FIG. 6 shows the results of western blots using total cell lysates, demonstrating similar expression levels of these proteins. These results clearly indicate that the binding of ANK peptide to SNCG interrupted the interaction of SNCG with BubR1.

Figure 7:
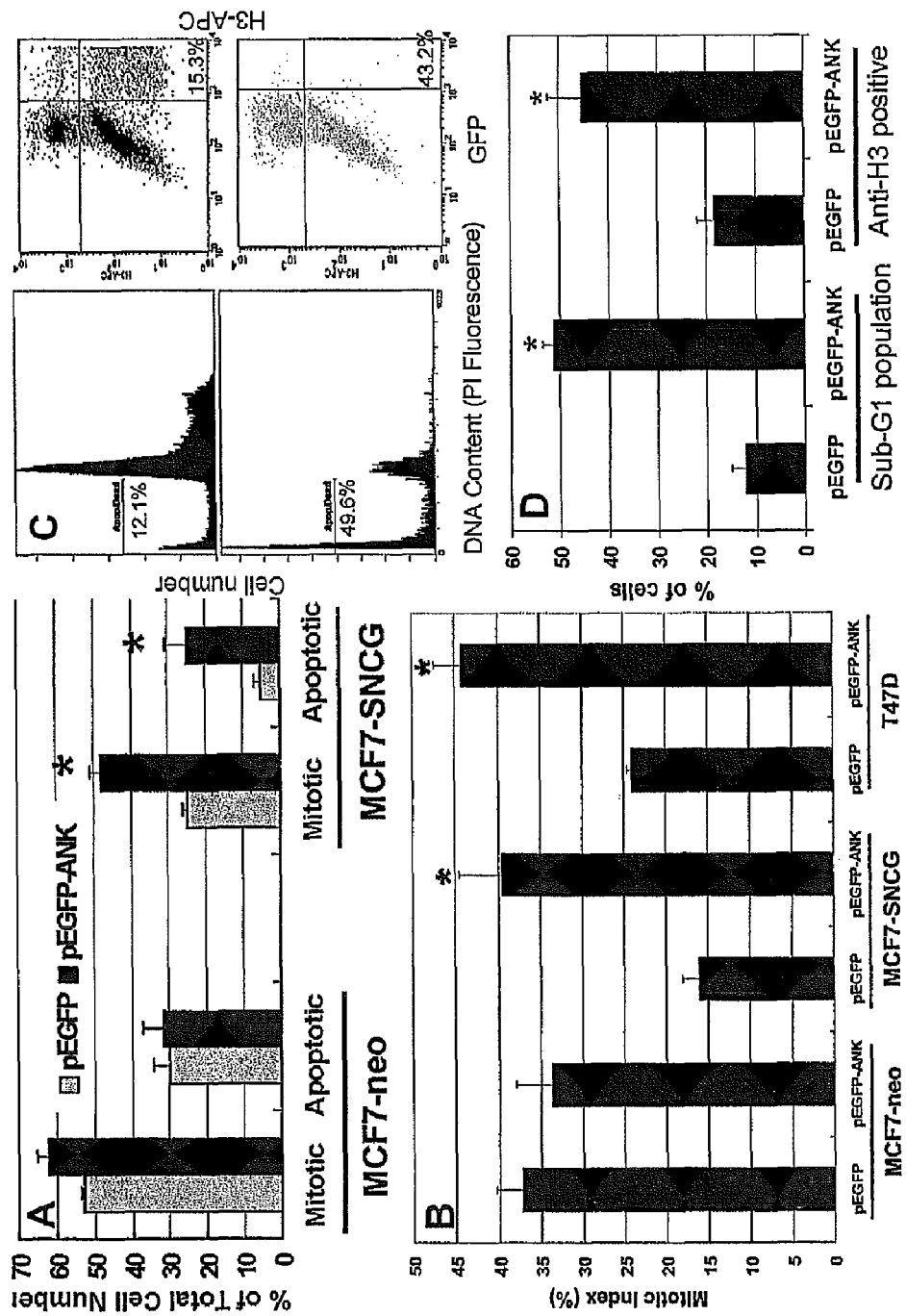
FIG. 7A through D show expression of EGFP-ANK disrupting the SNCG-mediated inhibition of mitotic checkpoint function as measured by microscopy and flow cytometry. The bar graphs show the expression of EGFP-ANK disrupting the SNCG-mediated inhibition of mitotic checkpoint function, using (FIG. 7A) DAPI and (FIG. 7B) anti-phospho-$H^3$ staining. For graphs of FIGS. 7A and 7B, the cells treated with 0.5 µM paclitaxel for 18 hours or untreated control cells were fixed with 4% paraformaldehyde for 20 minutes at room temperature. In both cases, the cells were then stained with 1 µg/ml of DAPI or 2 µg/ml anti-phospho-H3 primary and Texas Red goat anti-rabbit secondary antibodies (Invitrogen). Green fluorescent cells were identified for positive transfected cells. For each sample, 200-300 cells randomly chosen from 5 different views under a Nikon fluorescent microscope were scored for interphase, mitotic, or apoptotic based upon nuclei morphology. The data shown were derived from three separate transfections ($p<0.01$).

To further demonstrate the function of the ANK peptide in restoring the impaired mitotic checkpoint control in SNCG expressing cells, MCF7-neo, MCF7-SNCG and T47D cells were transfected with pEGFP-ANK or the control vector PEGFP. Two days after transfection, cells were exposed to paclitaxel for 18 hours and numbers of mitotic arrested and apoptotic cells were counted after DAPI staining. Expression of EGFP-ANK in neo cells did not significantly alter the mitotic index or the percentage of apoptotic cells. However, expression of this peptide in SNCG cells consistently caused an approximate 2-fold increase in the number of mitotic arrested cells and a 5-fold increase in apoptotic cell populations (FIG. 7A). These cells were also probed with rabbit polyclonal anti-phospho-$H^3$ and the mitotic index was calculated according to the proportion of the number of $H^3$ stained EGFP positive cells to total EGFP positive cells (FIG. 7B). This result corroborated with increases in sensitivity to paclitaxel by over-expressing EGFP-ANK in MCF7-SNCG and T47D cells shown by DAPI stained cells. Similar results were achieved using flow cytometric analysis of EGFP-ANK containing MCF7-SNCG cells treated with 0.5 μM paclitaxel. Cell cycle analysis of MCF7-SNCG cells transfected with EGFP-ANK revealed almost a four-fold increase in apoptotic/dead cell population in comparison to cells transfected with the control vector pEGFP (FIGS. 7C-D). Furthermore, anti-phospho-$H^3$ staining showed a 3,5-fold increase in positive phosphorylated histones in comparison with MCF7-SNCG cells not containing EGFP-ANK (FIG. 7C-D). Taken together these results confirmed the finding that overexpression of EGFP-ANK improves the sensitivity of MCF7 breast cancer cells to anti-microtubule drug treatment.

Figure 8:
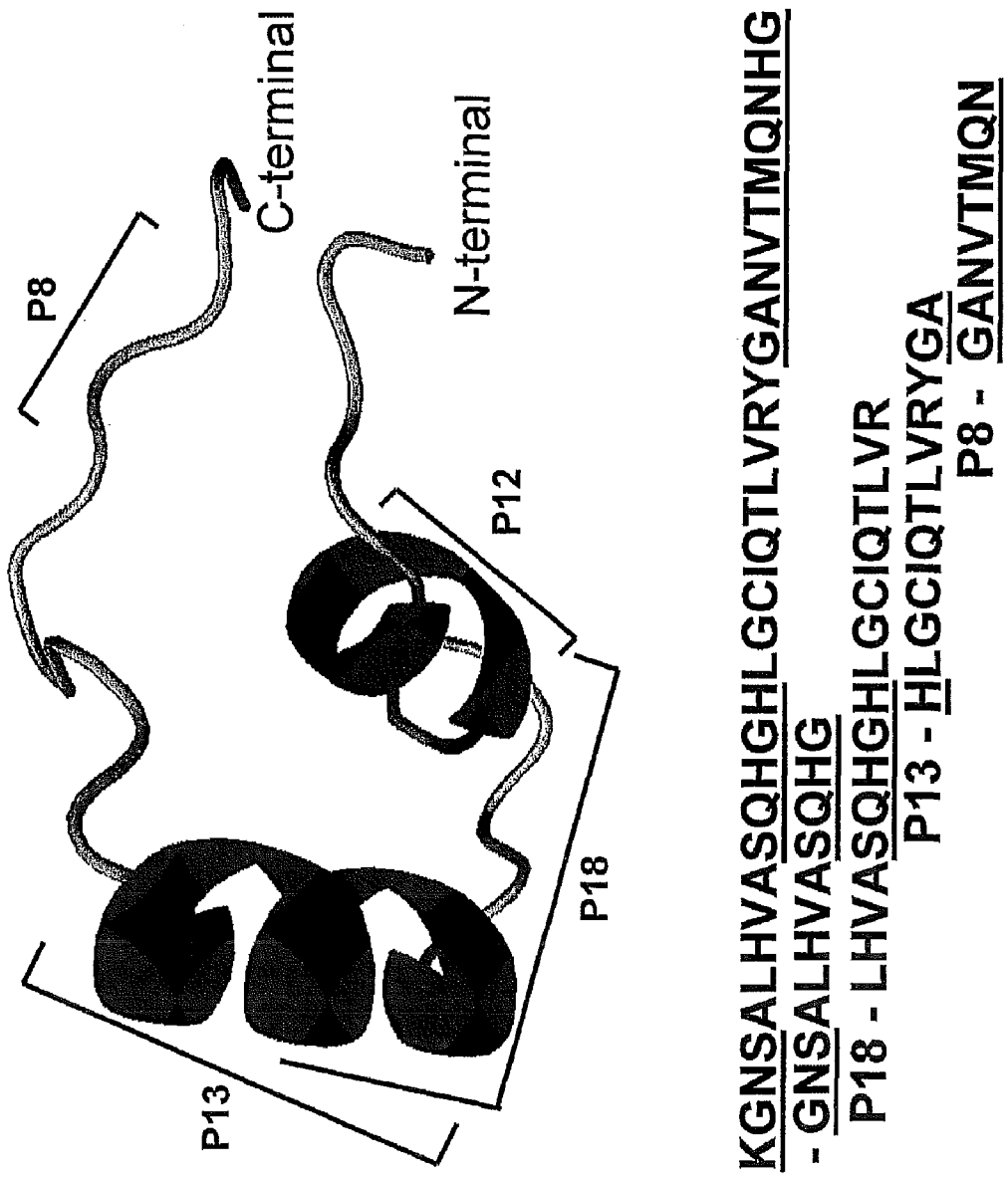
FIG. 8 provides a structural model of ANK as well as the amino acid sequence of the ANK peptide (SEQ ID NO:1) and exemplary peptides P12 (SEQ ID NO:2), P18 (SEQ ID NO:3), P13 (SEQ ID NO:4) and P8 (SEQ ID NO:5) comprising portions thereof. Amino acids of each peptide sequence residing in the structured or helical region of the structural model are depicted by letters not underlined, while amino acids of each peptide residing in the unstructured portion of the structural model are depicted by underlined letters.

Exemplary deletion peptides of EGFP-ANK were designed based on a molecular model of ANK peptide (SEQ ID NO:1) generated using the online web server swissmodel with the extension expasy.org/ of the world wide web. See FIG. 8. These exemplary deletion peptides are depicted FIG. 8 and in Table 2 below.

Figure 9:
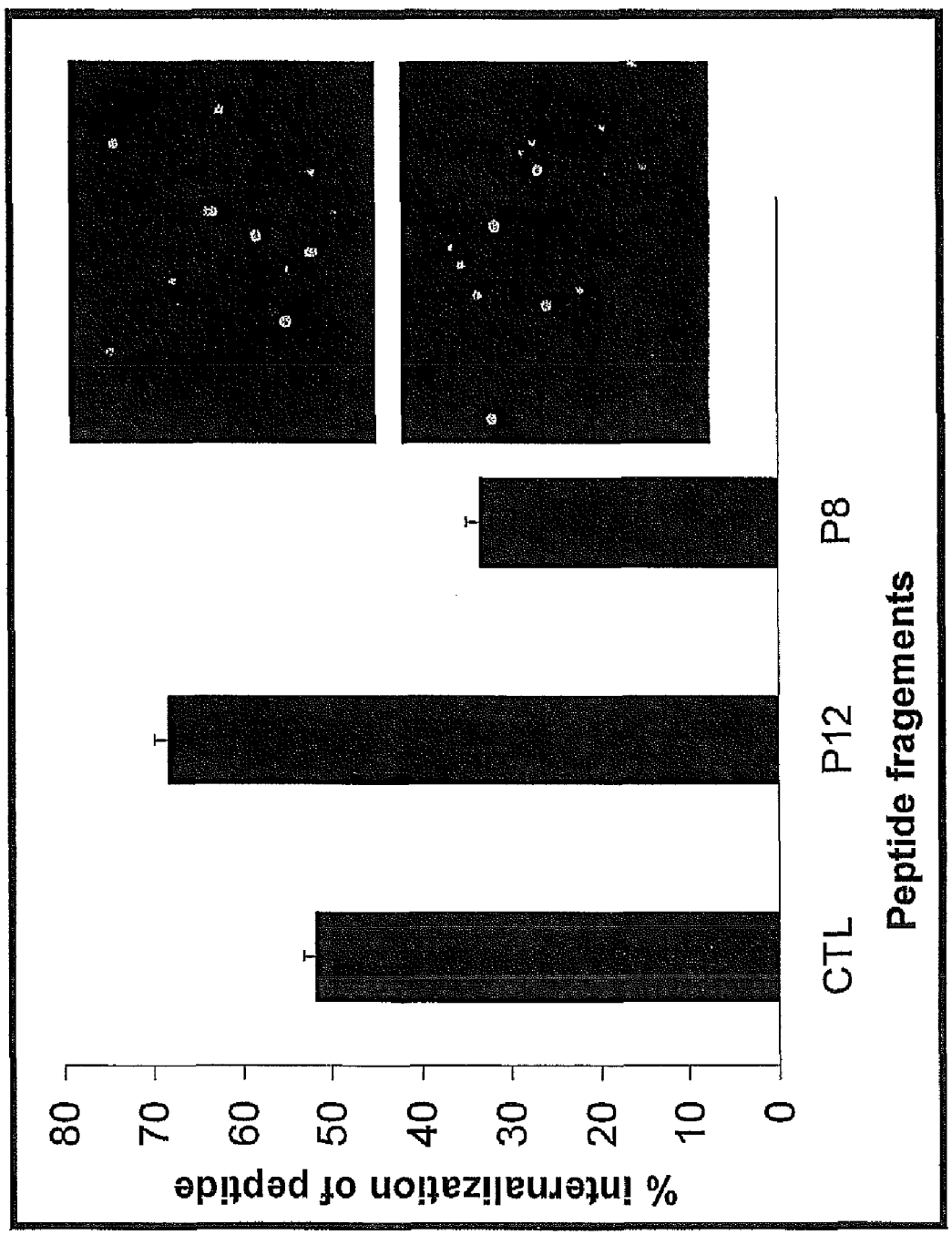
FIG. 9 shows results from experiments measuring the amount of carrier (TAT) tagged ANK peptides P12 and P8 permeabilized by cancer cells. Active internalization of peptides P8 and P12 was observed using fluorescent microscopy. Carrier tagged ANK peptide P8 permeabilized by cancer cells are depicted in the photograph on the upper right hand side of FIG. 9. Carrier tagged ANK peptide P12 permeabilized by cancer cells are depicted in the photograph on the lower right hand side of FIG. 9. Active internalization was also quantified and compared to a control using flow cytometry. Results are shown in the bar graph.
Figure 10:
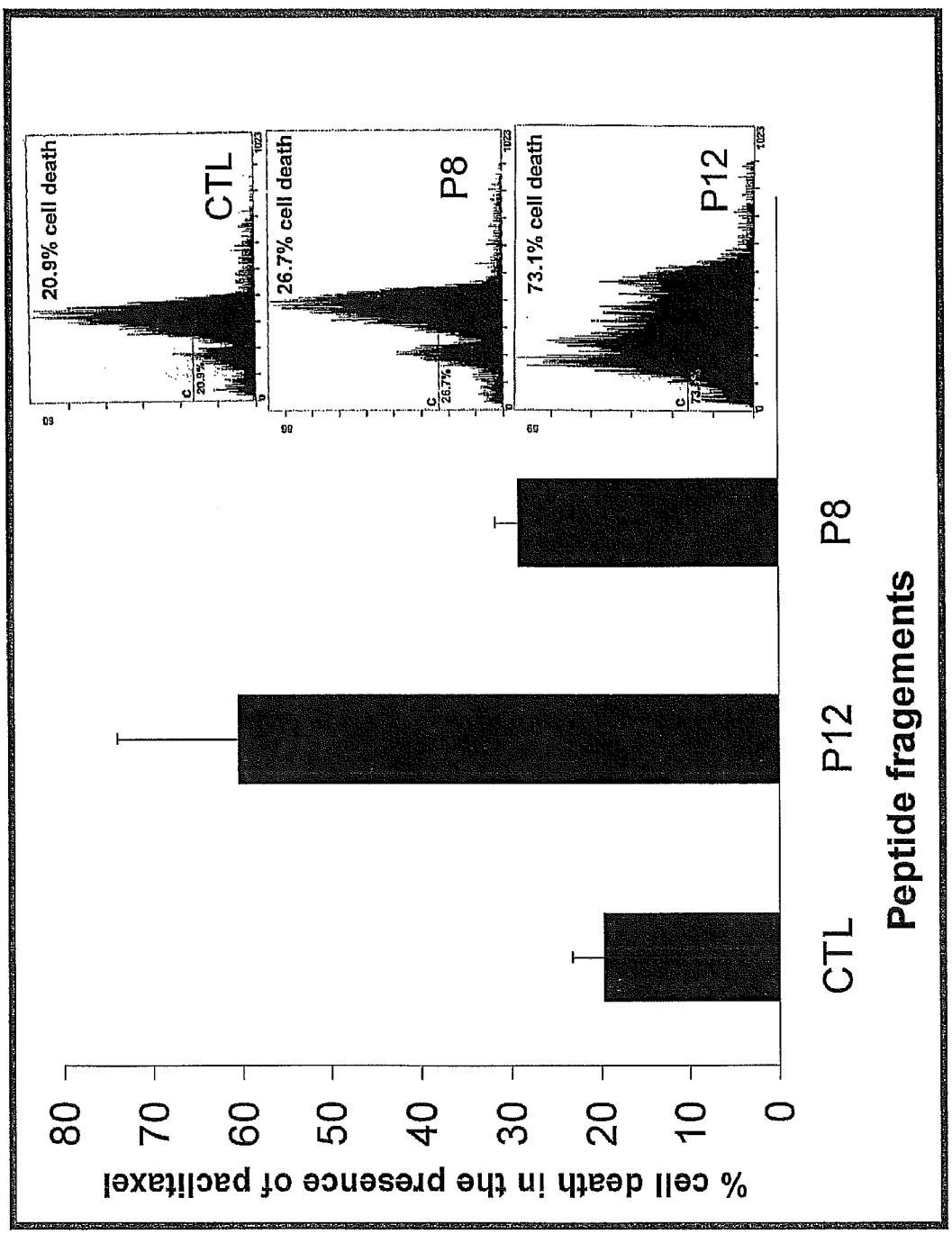
FIG. 10 shows results from experiments performed to assess the release of SNCG-mediated drug resistance in the presence of paclitaxel. In these experiments, cell death was quantified by assessing cell cycle of RNase-treated, PI-stained cells using flow cytometry. As shown in the bar graph, a significant amount of paclitaxel induced cell killing was observed in T47D cells while carrying ANK peptide P12 in comparison to control. Scans on the right-hand side of FIG. 10 are representative of the stages of cell cycle. The sub G1 population, shown in the left region of each scan, depicts the percent death.

ID NO:31) and a control peptide GYGRKKRRQRRR (TAT CTL; SEQ ID NO:29) were chemically synthesized. Each peptide contained FITC on its N-terminal end. These peptides were dissolved in 2% DMSO in PBS (pH 7.3) and applied directly on the Petri dish containing cancer cells (T47D) at a concentration of 10 μM. Active internalization of peptide was observed using fluorescent microscopy and was quantified using flow cytometry. Three independent experiments were performed with duplicates of each condition. FIG. 9 demonstrates the amount of carrier tagged ANK peptides permeabilized by the cancer cells. A similar experiment was also performed to assess release of SNCG-mediated drug resistance in the presence of paclitaxel. FIG. 10 shows a significant amount of paclitaxel-induced cell killing in the T47D cells in the presence of P12 peptide as compared to T47D cells in the presence of TAG CTL peptide.

Similar experiments were performed using liposome encapsulated P12 and P8 peptides with FITC on their N-terminal ends. For the liposome (100-200 nm size) formulation, 67 mg of palmitoyl-oleyl phosphatidylcholine (POPC) and 4.83 mg of cholesterol were mixed and then dissolved in 1 ml of chloroform. The mixture was dried under a stream of nitrogen gas. Dried lipids were rehydrated using P8 or P12 peptide (1 mg/ml) dissolved in phosphate-buffered saline (PBS) containing sodium cholate (53.75 mg) by vigorous vortexing of the mixture overnight at 4° C. Aqueous solutions of P8 or P12 peptide were then dialysed extensively in PBS to

TABLE 2

| ANK Peptide: | KGNSALHVASQHGHLGCIQTLVRYGANVTMQNHG | (SEQ ID NO: 1) |
|---|---|---|
| Del. Pep. P12 | GNSALHVASQHG | (SEQ ID NO: 2) |
| Del. Pep. P18 | LHVASQHGHLGCIQTLVR | (SEQ ID NO: 3) |
| Del. Pep. P13 | HLGCIQTLVRYGA | (SEQ ID NO: 4) |
| Del. Pep P8 | GANVTMQN | (SEQ ID NO: 5) |

These exemplary deletion peptides were amplified by PCR using respective primers as set forth in Example 11 and directionally cloned into the EcoRI site of EGFP-C2 to produce EGFP-ANK deletion peptides. The resulting plasmid was sequenced to verify the correct inframe ligation and right orientation of the deletion peptide. Cytoplasmic expression of EGFP-ANK deletion peptide was confirmed by green fluorescent signals in cells transfected with pEGFP-ANK deletion peptides. The correct molecular masses of the EGFP-ANK deletion peptides were verified by western blotting with anti-GFP antibody.

Transfection and co-immunoprecipitation was performed as described in Example 11. MCF7-neo and MCF7-SNCG clones were transfected with pEGFP-ANK deletion peptide P8, P12, P13 or P18 plasmids or the control plasmid pEGFP by FuGENE 6 transfection reagent (Roche). Two days after transfection, cells were lysed and co-IP was performed, and results were analyzed using western blotting by anti-EGFP and anti-SNCG antibodies. SNCG was identified to interact with EGFP-ANK deletion peptide P12, residues 2-13 of ANK peptide: GNSALHVASQHG (SEQ ID NO:2), and P8, residues 25-32 of ANK peptide: GANVTMQN (SEQ ID NO:5).

Figure 11:
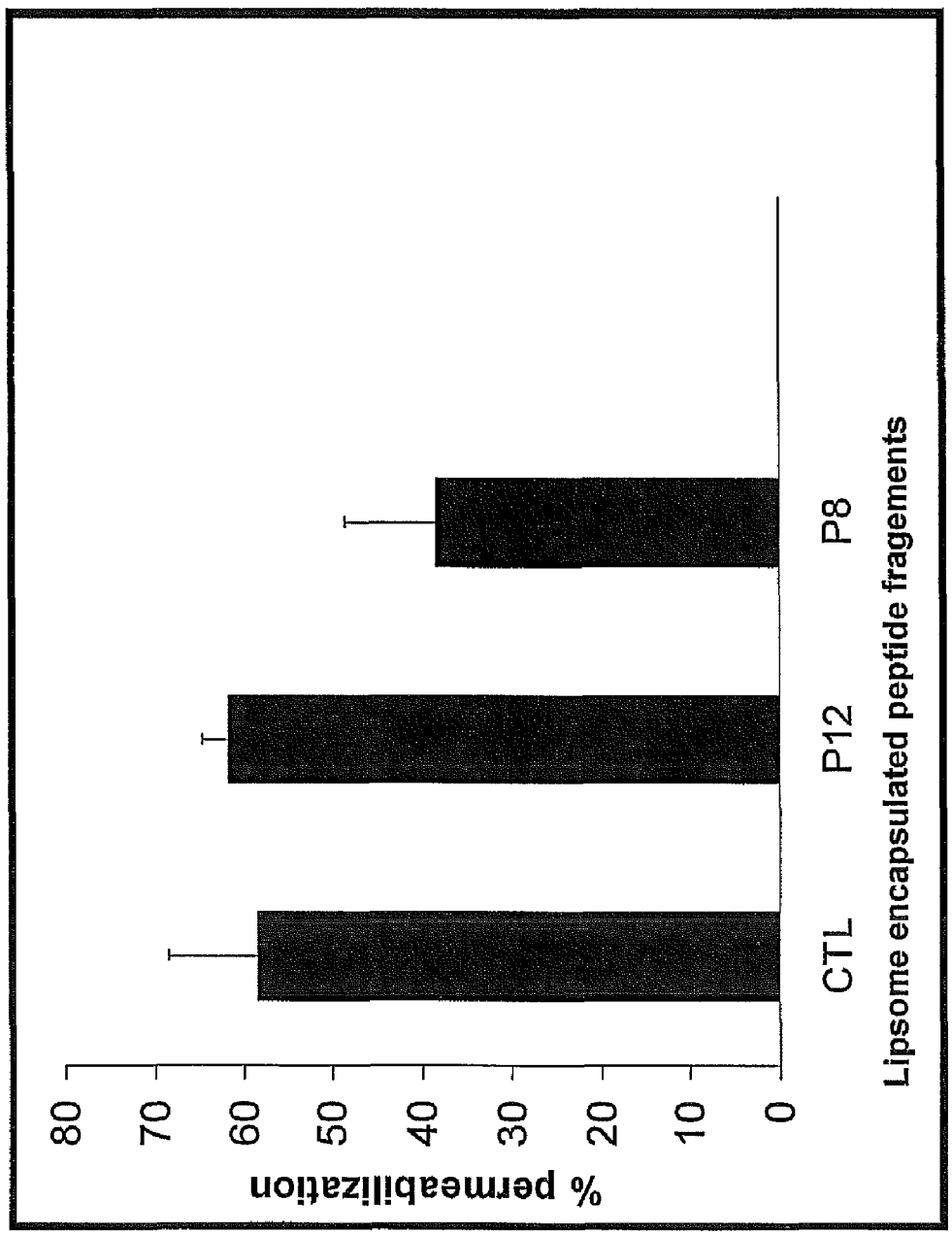
FIG. 11 shows results of active internalization of liposome encapsulated carrier tagged ANK peptides P12 and P8 as compared to a control peptide (CTL) as observed by microscopy. The green cells positive for ANK peptide internalization were counted from five different views under a fluorescent microscope, averaged and presented in the bar graph.

Carrier tagged ANK peptide fragments were applied directly and in liposomes to release SNCG-mediated drug resistance. For these experiments, GYGRKKRRQRRR (TAT) tagged GNSALHVASQHG (P12) (SEQ ID NO:30), GYGRKKRRQRRR (TAT) tagged GANVTMQN (P8) (SEQ remove the sodium cholate molecules. These liposomes were applied directly on T47D cells to observe internalization of P8 or P12 peptide and cell killing in the presence of paclitaxel. FIG. 11 shows active internalization of liposome-encapsulated P8 or P12 peptides as observed by microscopy. The green cells positive for peptide internalization were counted from five different views under a fluorescent microscope, averaged and presented in the bar graph (FIG. 11).

Accordingly, these experiments demonstrate for the first time a single ankyrin repeat-like motif peptide interacting with a protein. As shown herein, the 34-amino acid ANK peptide, design of which was based on the conserved residues of a single ankyrin repeat-like motif, binds to the native SNCG intracellularly prohibiting the interaction of SNCG with BubR1 and thereby releasing the inhibitory effect of SNCG on BubR1-mediated mitotic checkpoint function. BubR1 can prevent the uncontrolled cell division observed in highly infiltrating breast cancers and therefore, is a desired target for controlling these cancers. Cells not expressing BubR1 are able to override mitotic checkpoint controls and continue to progress through cell cycle (Taylor, S. S, and McKeon, F. Cell 1997 89:727-735). This is a very important inhibitory activity as various types of cancers have mitotic checkpoint defects which in some cases are believed to be caused by silencing of BubR1 through mutations (Ohshima et al. Cancer Lett. 2000 158:141-150). Since BubR1 is a critical component of the mitotic checkpoint control, it is believed to be a cellular target of oncogenic proteins such as SNCG that induce tumor progression. Given that the SNCG-BubR1 interaction is the demonstrated leading factor that overrides the effect of antimicrotubule drugs such as nocodazole (Gupta et al. Oncogene 2003 22:7593-7599), minimization of this interaction is desired. The observed ANK peptide binding with SNCG, and the resultant competition with the SNCG-BubR1 interaction in vitro and in vivo identified by the inventors herein provides a novel means by which sensitivity of cancer cells to anti-microtubule drugs can be increased. The ability of this peptide to associate with SNCG is also indicative of its ability to inhibit SNCG stimulation of ER-α signaling and hormone responsive tumorigenesis as well as drug resistance to estrogen receptor modulators such as tamoxifen.

In addition to the above-described in vitro and in vivo assays, efficacy of the peptides of the present invention to potentiate efficacy of anticancer drugs can be confirmed in a mouse model. In these experiments, cells such as MCF7-SNCG or T47D cells are suspended in buffered saline (10,000-20,000 cells) stably overexpressing EGFP-ANK and injected into the abdominal mammary-gland area of 5-6-week old female athymic nude mice (N=5) implanted with a 0.25 mg estrogen pellet. Control mice receive an equal number of cells containing only EGFP. Measurement of tumor size (three-dimensional measurements (in millimeters)) is carried out at weekly intervals using an electronic caliper. When the tumor reaches 4-5 mm in size, both groups of mice are administered intraperitoneal injections of paclitaxel (Sigma) at a dose of 600 μg/mouse (1.5 μg/μl) for two weeks. Post-treatment mice are sacrificed, tumor sizes are measured and histopathology of tumors is performed.

The ability of ANK association with SNCG to alleviate hormone responsive tumorigenesis can be confirmed in, for example, SNCG positive breast cancer cells. For these experiments, the association of SNCG and ER-α is first established. This can be done by transfecting MCF12A cells with pCI-SNCG, performing co-IP using an anti-SNCG antibody, and looking for ER-α pull down via western blotting. This experiment is then repeated in the presence of EGFP-ANK peptide to assess the inhibition of SNCG association with ER-α. Further to this, experiments are performed to assess cell killing in MCF12A cells in the presence and absence of estrogen. MCF12A cells are co-transfected with pCI-SNCG and EGFP-ANK peptide. Control cells receive only pCI-SNCG. Cells are grown in the presence and absence of estrogen and treated with tamoxifen (2 μM) for 24 hours. Cell death in these cultures is then estimated using flow cytometry and microscopy as described herein.

The present invention thus relates to synthetic peptides comprising at least one ankyrin repeat-like motif or a portion thereof or mimetic thereof which interact with SNCG to reduce SNCG-mediated resistance to treatment with anticancer drugs and/or to inhibit tumorigenesis and/or proliferation of cancer cells. The prominent expression of SNCG in multiple types of human cancers is indicative of these peptides or a portion thereof or a mimetic thereof having a broad effect in cancer metastasis and patient responses to anti-cancer drugs in many types of cancer.

The consensus sequence of the 33 residue ankyrin repeat contains a number of "signature" residues that define the shape of the repeat (Mosavi et al. Protein Science 2004 13:1435-1448). These include a TPLH (SEQ ID NO:6) motif at positions 4 through 7; glycines at positions 13 and 25; and nonpolar residues at positions 6, 8, 9, 10, 17, 18, 20, 21 and 22 (Mosavi et al. Protein Science 2004 13:1435-1448). Accordingly, by the phrase "at least one ankyrin repeat-like motif" as used herein, it is meant a peptide comprising an amino acid sequence with conserved amino acid residues from the consensus sequence of a single ankyrin repeat. Accordingly, peptides of the present invention comprise one or more of the following conserved amino acid residues:

a threonine at position 4;
a proline at position 5;
a leucine at position 6;
a histidine at position 7;
a glycine at positions 13 or 25; and/or
a nonpolar residue at positions 6, 8, 9, 10, 17, 18, 20, 21 and/or 22. More preferably the peptides of the present invention comprising at least one ankyrin repeat-like motif comprise one or more of the following conserved amino acid residues:

a glycine at positions 2, 13 and/or 25;
a threonine at position 4;
a proline at position 5;
a leucine at positions 6 and/or 21;
a histidine at positions 7 and/or 14; and/or
an alanine at positions 9 and/or 26.

More preferably, the peptide comprises at least one ankyrin repeat-like motif with the sequence $GX_1X_2X_3LHX_4AX_5X_6X_7GHX_8X_9X_{10}$ $X_{11}X_{12}X_{13}$ $LX_{14}X_{15}X_{16}GA$ (SEQ ID NO: 7) or $GX_1X_2X_3LHX_4$ $AX_5X_6X_7$ $GHX_8X_9X_{10}X_{11}X_{12}X_{13}LX_{14}X_{15}X_{16}GAX_{17}$ $X_{18}NX_{19}X_{20}X_{21}X_{22}$ (SEQ ID NO:32), where $X_1$ is B1 or N; $X_2$ is B2; $X_3$ is B1; $X_4$ is B1 or Q; $X_5$ is B1 or B2; $X_6$ is B2 or K; $X_7$ is B2 or V; $X_8$ is B1 or K; $X_9$ is B3 or B4; $X_{10}$ is I or C; $X_{11}$ is B1; $X_{12}$ is B1, B2 or R; $X_{13}$ is B1 or B4; $X_{14}$ is B1 or T; $X_{15}$ is B2, B3 or R; $X_{16}$ is B1, B2 or E; $X_{17}$ is B1, B2 or E; $X_{18}$ is B1, B2 or D; $X_{19}$ is B1 or B2; $X_{20}$ is B1 or B3; $X_{21}$ is B1 or B2; $X_{22}$ is B1, B2 or E; B1 is G, A, V, L, I, M, F, W, or P; B2 is S, T, C, Y, N, or Q; B3 is D or E; and B4 is K, R or H; or a portion thereof. More preferred is ANK peptide KGNSAL-HVASQHGHLGCIQTLVRYGANVTMQNHG (SEQ ID NO:1) or a portion or mimetic thereof.

By "portion thereof" it is meant to be inclusive of peptides exhibiting similar biological activities to the ANK peptide described herein but which, (1) comprise shorter fragments of the 34 residue ANK peptide or another ankyrin repeat-like motif peptide of the present invention, or (2) overlap with only part of the 34 residue ANK peptide or another ankyrin repeat-like motif peptide of the present invention. For example, experiments with deletion peptides showed shorter peptides of 12 amino acids (residues 2-13 of ANK peptide: GNSALHVASQHG (SEQ ID NO:2)) and 8 amino acids (residues 25-32 of ANK peptide: GANVTMQN (SEQ ID NO:5)) to exhibit similar interaction with SNCG and reduce SNCG-mediated resistance to treatment with anticancer drugs to the ANK peptide. Accordingly, in a preferred embodiment, by portion thereof, it is meant a peptide of the present invention comprising part, preferably at least 8 to 12 amino acid residues, at or near the N terminus and/or C terminus of an ankyrin repeat-like motif peptide. By "at or near" it is meant to include peptides containing the N-terminal or C-terminal amino acid as well as peptides which do not contain the N-terminal or C-terminal amino acid. For example, peptides P12 and P8, both of which are demonstrated herein to exhibit similar biological activities to ANK peptide, do not include the N-terminal or C-terminal amino acid, respectively.

By "synthetic", as used herein it is meant that the peptide or portion thereof is prepared synthetically either by chemical means or recombinantly.

Further, it will of course be understood, without the intention of being limited thereby, that a variety of substitutions of amino acids in the disclosed ANK peptide is possible while preserving the structure responsible for its interaction with SNCG and it reduction of SNCG-mediated resistance to treatment with anticancer drugs and/or inhibition of tumorigenesis and/or cancer cell proliferation. For example, substitution of one or more amino acids of the ANK peptide with one or more amino acids of the ankyrin repeat consensus sequence(s) or one or more other ankyrin-like repeats such as set forth in Table 3 is expected to produce a peptide with similar biological activity to the ANK peptide and thus is encompassed within the scope of the present invention.

TABLE 3

```
ank-like 1       NGNNLLHIAASQGHAHCLQHLTSLMGEDCLNER      (SEQ ID NO: 8)
ank-like 2       KKLTPAGLAIKNGQLECVRWMVSETEAIAELSC      (SEQ ID NO: 9)
ank-like 3       DEPSLIHVAGCVGQKKILLWLLQFMQEQGISLD      (SEQ ID NO: 10)
ank-like 4       DGNSAVHVASQHGYLGCIQTLVEYGANVTMQNH      (SEQ ID NO: 11)
ankyrin          ---TPLH-----G-----------G--------
repeat^a ANK peptide      KGNSALHVASQHGHLGCIQTLVRYGANVTMQNHG     (SEQ ID NO: 1)
mc ank           -G-TPLH-AA--GH---V--LL--GA--N----
repeat^b
```

[a] as disclosed by Mosavi et al. (Protein Science 2004 13:1435-1448).
[b] mammalian consensus for ankyrin repeat as disclosed by Engelender et al. (Nat. Genet. 1999 22:110-114) wherein conserved residues aligned with ankyrin-like repeats of synphilin-1 are indicated by italics and identical residues are indicated by bolding.

Conservative substitutions are also described in the patent literature, as for example, in U.S. Pat. No. 5,264,558. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could possibly be made, as could substitutions among the charged basic amino acids, lysine and arginine. Substitutions among the aromatic amino acids, including phenylalanine, histidine, tryptophan and tyrosine would also likely be possible. In some situations, histidine and basic amino acids lysine and arginine may be substituted for each other. These sorts of substitutions and interchanges are well known to those skilled in the art and encompassed within the scope of the ankyrin repeat-like motif peptides of the present invention.

Also preferred for use in the present invention to interact with SNCG and reduce SNCG-mediated resistance to treatment with anticancer drugs and/or inhibit tumorigenesis and/or cancer cell proliferation are compositions with a formula of Y-Z or Q-Y-Z. In these compositions Z is linked to Y and/or Q is linked to Y-Z via any acceptable binding means and selected based upon selection of Z or Q. Examples of acceptable binding means include, but are in no way limited to, covalent binding, noncovalent binding, hydrogen binding, antibody-antigen recognition and ligand binding. In compositions with the formula Y-Z or Q-Y-Z, Y comprises at least one ankyrin repeat-like motif peptide or a portion thereof or mimetic thereof; Z comprises a compound linked to Y that enhances the performance of Y; and in embodiments comprising Q, Q may be identical to Z or different from Z and also enhances performance of the compound Q-Y-Z.

Exemplary Z or Q compounds include, but are not limited to, a targeting agent, a second agent for treatment of cancer, an agent which enhances solubility, absorption, distribution, half-life, bioavailability, stability, activity and/or efficacy, or an agent which reduces toxicity or side effects of the compound. By targeting agent it is meant to include agents which direct the composition to the tumor as well as agents which enhance or increase entry of the composition into the tumor cell itself.

Exemplary targeting agents of Z and/or Q include, but are in no way limited to, antibodies and active fragments thereof such as, for example, Fab fragments, peptides, hormones, vitamins, lectins, saccharides, carbohydrates and other ligands that have affinity for cells of interest and/or aid in transport into cells of interest. Preferably, the targeting agent does not influence pharmacokinetics of Y, the Y-Z or Q-Y-Z composition and/or the delivery vehicle.

Examples of targeting peptides useful in these compositions include, but are not limited to, the TAT peptide derived from the HIV-1 TAT protein which facilitates intracellular delivery of proteins and small colloidal particles; the antennapedia protein from *Drosophila*; the VP22 protein from the herpes simplex virus; transportan and polyarginine; the RGD motif; and the NGR peptide (CNGRCGGklaklakklaklak-NH2 (Disulfide bridge: 1-5)). The NGR peptide binds an aminopeptidase (CD13) isoform expressed in tumor blood vessels. Peptides containing the Asn-Gly-Arg (NGR) motif, including both linear GNGRG and disulfide-bridged CNGRC, have been disclosed to be useful for delivering various viral particles and anti-tumor compounds, such as chemotherapeutic drugs, apoptotic peptides, cytokines, cytotoxic drugs, proapoptotic peptides, and tumor necrosis factor (TNF), to tumor blood vessels (Ellerby et al. Nature Medicine 1999 5:1032; Colombo et al. J. Biol. Chem. 2002 277 (49): 47891; Van Hensbergen et al. Biochem. Pharmacol. 2002 63(5):897 (2002); Plesniak et al. Protein Science 2004 13:1988; Curnis et al. Cancer Research 2002 62:867; Curnis et al. J. Clin. Invest. 2002 110(4):475). Exemplary targeting peptides useful in these compositions of the present invention are also described in Schwartz and Zhang (Current Opinion in Molecular Therapeutics 2000 2:162-167), teachings of which are herein incorporated by reference in their entirety.

Alternatively, Y of the Y-Z or Q-Y-Z compositions of the present invention can be conjugated with a hydrophilic polymer such as, but not limited to, polyethylene glycol (PEG) to improve stability and longevity in circulation, to improve permeability into tumor vasculature and interstitial tumor space, and to improve longevity once reaching the interstitial space.

Alternatively, Y of the Y-Z or Q-Y-Z compositions of the present invention can be chemically conjugated to the Fc domain of human gamma immunoglobulin (IgG) or to albumin.

Cell penetrating peptides (CPPs) or peptide transduction domains (PTDs) can also be attached to Y of the Y-Z or Q-Y-Z compositions of the present invention to enhance intracellular delivery. Exemplary CPPs include Tat PTD derived from the HIV Tat protein, Antennapedia (also known as Antp or penetratin), VP22 (a herpes virus protein), model amphipathic peptide (MAP), transportan, transportan-10, KALA, and Pep-1.

Further, vector molecules such as lytic peptides, pH-sensitive polymers or swellable dendritic polymers can be attached to Y of the Y-Z or Q-Y-Z compositions of the present invention as a targeting agent to enhance endosomal escape if internalization is via endocytosis (Torchilin and Lukyanov (2003) Drug Discovery Today 8(6): 259-266).

Many of these targeting agents are commercially available and can be readily linked to Y of the Y-Z or Q-Y-Z compositions of the present invention.

By "mimetic", as used herein, it is meant to be inclusive of peptides, which may be recombinant, and peptidomimetics, as well as small organic molecules, which exhibit similar or enhanced interaction with SNCG and reduction of SNCG-mediated resistance to treatment with anticancer drugs and/or inhibition of tumorigenesis and/or cancer cell proliferation as compared to the ankyrin repeat-like motif peptides of the present invention. These include peptide variants which comprise conservative amino acid substitutions relative to the sequences of the ankyrin repeat-like motif peptides exemplified herein and peptide variants which have a high percentage of sequence identity with the ankyrin repeat-like motif peptides exemplified herein. By high percentage of sequence identity it is meant a peptide which shares at least 60%, more preferably at least 65%, more preferably at least 70%, more preferably at least 75%, more preferably at least 80%, more preferably at least 85%, more preferably at least 90%, more preferably at least 95%, and more preferably at least 99% sequence identity with ANK peptide or an exemplified ank-like peptide or portion thereof. For peptides sharing sequence identity with a portion of the ANK peptide or the exemplary ank-like peptides exemplified herein, it is preferred that a higher sequence identity be shared with either the N-terminus or the C-terminus of the peptide. Variant peptides can be aligned with the reference peptide or portion thereof to assess percentage sequence identity in accordance with any of the well-known techniques for alignment. For example, a variant peptide greater in length than a reference peptide is aligned with the reference peptide using any well known technique for alignment and percentage sequence identity is calculated over the length of the reference peptide, notwithstanding any additional amino acids of the variant peptide, which may extend beyond the length of the reference peptide. A variant peptide shorter in length than the reference peptide is aligned with the reference peptide at the region of shared homology, i.e. the C terminus, N terminus or the central region of the reference peptide.

Preferred variants include, but are not limited to, peptides comprising one or more D amino acids, which are equally effective but less susceptible to degradation in vivo, and cyclic peptides. Cyclic peptides can be circularized by various means including but not limited to peptide bonds, lactam rings, depsicyclic terminal residues (i.e. a disulfide bond) and/or N-terminal to C-terminal head-to-tail cyclization.

The stability of ANK peptides and variants thereof of the present invention can also be enhanced by modifications to the peptide or variant including, but not limited to, acetylation, glycosylation, amidation, and/or addition of unnatural amino acids such as β-amino and α-trifluoromethyl amino acids to the ANK peptide or variant thereof.

As used herein, the term "peptidomimetic" is intended to include peptide analogs that serve as appropriate substitutes for the ankyrin repeat-like motif peptides, in interacting with SNCG and reducing SNCG-mediated resistance to treatment with anticancer drugs and/or inhibiting tumorigenesis and/or cancer cell proliferation. The peptidomimetic must possess not only similar chemical properties, e.g. affinity to SNCG, but also efficacy and function. That is, a peptidomimetic exhibits function(s) of an ankyrin repeat-like motif peptide, without restriction of structure. Peptidomimetics of the present invention, i.e. analogs of an ankyrin repeat-like motif peptide, include amino acid residues or other moieties which provide the functional characteristics described herein. Peptidomimetics and methods for their preparation and use are described in Morgan et al. 1989, "Approaches to the discovery of non-peptide ligands for peptide receptors and peptidases," In Annual Reports in Medicinal Chemistry (Vuirick, F. J. ed), Academic Press, San Diego, Calif., 243-253.

Mimetics of the present invention may be designed to have a similar structural shape to ankyrin repeat-like motif peptides but have enhanced activities. For example, conformationally restricted moieties such as a tetrahydroisoquinoline moiety may be substituted for a phenylalanine, while histidine bioisoteres may be substituted for histidine to decrease first pass clearance by biliary excretion. Peptidomimetics of the present invention may also comprise peptide backbone modifications. Analogues containing amide bond surrogates are frequently used to study aspects of peptide structure and function including, but not limited to, rotational freedom in the backbone, intra- and intermolecular hydrogen bond patterns, modifications to local and total polarity and hydrophobicity, and oral bioavailability. Examples of isosteric amide bond mimics include, but are not limited to, ψ[$CH_2S$], ψ[$CH_2NH$], ψ[$CSNH_2$], ψ[$NHCO$], ψ[$COCH_2$] and ψ[(E) or (Z)CH=CH].

Identification of the activity of the ankyrin repeat-like motif peptides also permits molecular modeling based on these peptides for design, and subsequent synthesis, of small organic molecules that interact with SNCG and reduce SNCG-mediated resistance to treatment with anticancer drugs and/or inhibit tumorigenesis and/or cancer cell proliferation. These small organic molecules mimic the structure and activity of the ankyrin repeat-like motif peptides. However, instead of comprising amino acids, these small organic molecules comprise bioisosteres thereof, substituents or groups that have chemical or physical similarities, and exhibit broadly similar biological activities.

Bioisosterism is a lead modification approach used by those skilled in the art of drug design and shown to be useful in attenuating toxicity and modifying activity of a lead compound such as the ANK peptide of SEQ ID NO:1, other ankyrin repeat-like motif peptides of SEQ ID NO: 8, 9, 10 or 11, of the ankyrin consensus peptide depicted in Table 3 and referred to therein as the ankyrin repeat.

Bioisosteric approaches are discussed in detail in standard reference texts such as The Organic Chemistry of Drug Design and Drug Action (Silverman, R B, Academic Press, Inc. 1992 San Diego, Calif., pages 19-23). Classical bioisosteres comprise chemical groups with the same number of valence electrons but which may have a different number of atoms. Thus, for example, classical bioisosteres with univalent atoms and groups include, but are not limited to: $CH_3$, $NH_2$, OH, F and Cl; Cl, $PH_2$ and SH; Br and i-Pr; and I and t-Bu. Classical bioisosteres with bivalent atoms and groups include, but are not limited to: —$CH_2$— and NH; O, S, and Se; and $COCH_2$, CONHR, $CO_2R$ and COSR. Classical bioisosteres with trivalent atoms and groups include, but are not limited to: CH═ and N═; and P═ and As═. Classical bioisosteres with tetravalent atoms include, but are not limited to: C and Si; and ═C⁺═, ═N⁺═and ═P⁺═. Classical bioisosteres with ring equivalents include, but are not limited to: benzene and thiophene; benzene and pyridine; and tetrahydrofuran, tetrahydrothiophene, cyclopentane and pyrrolidine. Nonclassical bioisosteres still produce a similar biological activity, but do not have the same number of atoms and do not fit the electronic and steric rules of classical isosteres. Exemplary nonclassical bioisoteres are shown in the following Table.

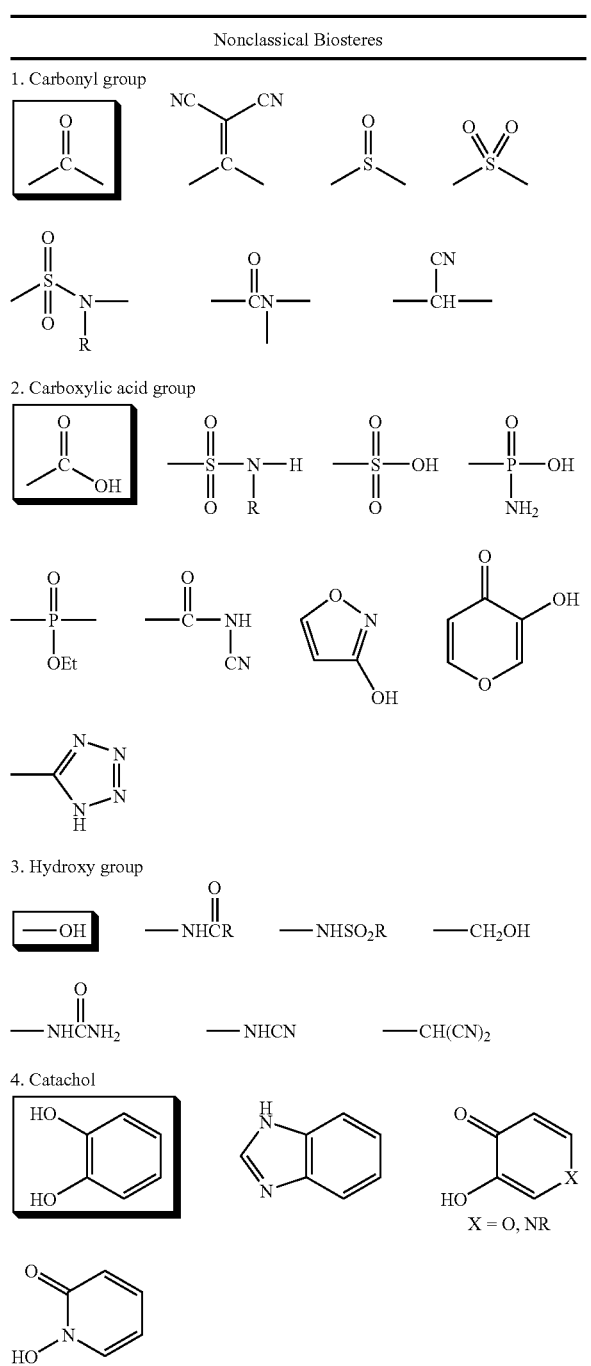

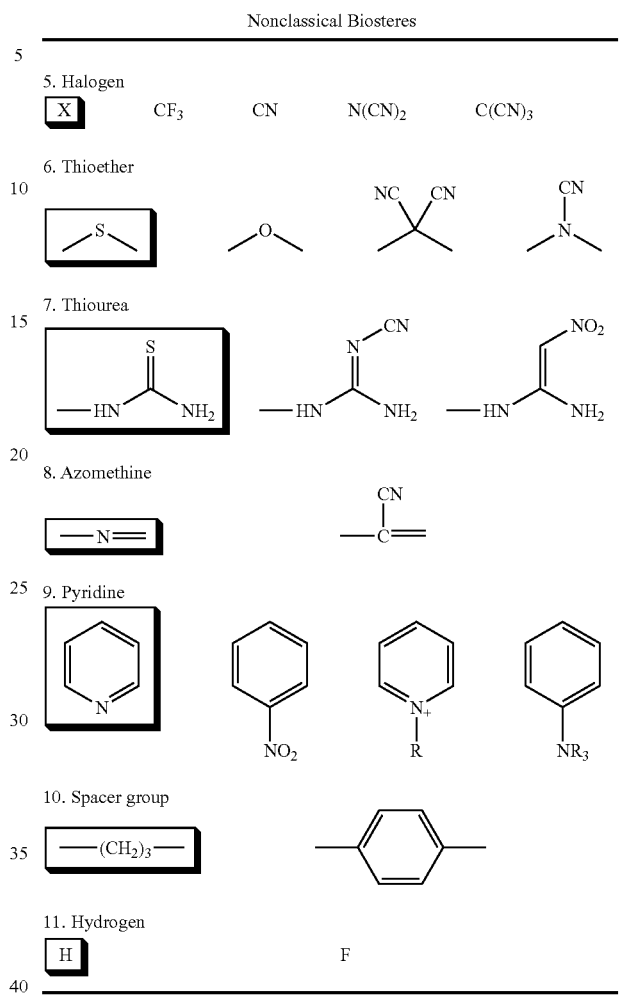

Additional bioisosteric interchanges useful in the design of small organic molecule mimetics of the present invention include ring-chain transformations.

A peptide or portion thereof, Y-Z or Q-Y-Z composition or mimetic thereof of the present invention is preferably formulated with a vehicle pharmaceutically acceptable for administration to a subject, preferably a human, in need thereof. Methods of formulation for such pharmaceutical compositions are well known in the art and taught in standard reference texts such as *Remington's Pharmaceutical Sciences*, Mack Publishing Co., Easton, Pa., 1985. A pharmaceutical composition of the present invention may comprise a single peptide or portion thereof, a Y-Z or Q-Y-Z composition, or a mimetic of these which interacts with SNCG and reduces SNCG-mediated resistance to treatment with anticancer drugs and/or inhibits tumorigenesis and/or cancer cell proliferation. These pharmaceutical compositions may be administered alone or in combination with a second anticancer drug or agent. For example, a pharmaceutical composition of the present invention comprising an ankyrin repeat-like motif peptide or portion thereof or mimetic thereof, can be administered to a subject in combination with a microtubule inhibitor. Microtubule inhibitors, also referred to as anti-microtubule drugs, such as, but not limited to vinca alkaloids and taxanes, are cytotoxic agents that inhibit cell growth by disrupting microtubules, thereby preventing cell division. Microtubule inhibitors are often used as first line chemotherapeutic agents in the treatment of metastatic cancers. Exemplary microtubule inhibitors include, but are not limited to, nocodazole, paclitaxel, colchicine, dolastatin 15, podophyllotoxin, rhizoxin, vinblastine, vincristine, vindesine and vinorelbine (Navelbine). Examples of commercially available taxanes include TAXOL (paclitaxel, Bristol-Myers Squibb), TAXOTERE (docetaxel, Sanofi-Aventis) and ABRAXANE (a reformulated nanoparticle albumin-bound (nab) paclitaxel, Abraxis BioScience). There are also anti-microtubule drugs currently in clinical development. Examples of taxanes in clinical trials for breast cancer include MAC-321 (Wyeth, Phase II), TOCOSOL® paclitaxel (Schering, Phase III) and TAXOPREXIN DHA-paclitaxel (Protarga, Phase III). Further, new taxanes, such as ABRAXANE involve new delivery methods that remove the need for traditional chemical solvents; they are anticipated to make significant inroads due to fewer side effects than traditional taxanes. There are also several approved combination treatments (for example, TAXOL-GEMZAR for the treatment of metastatic breast cancer and HERCEPTIN-TAXOTERE as a first-line therapy for HER2-positive metastatic breast cancer) that include anti-microtubule drugs.

Alternatively, the pharmaceutical composition of the present invention comprising an ankyrin repeat-like motif peptide or portion thereof or mimetic thereof, can be administered to a subject in combination with a hormonal cancer treatment. Exemplary hormonal cancer treatments include, but are not limited to, selective estrogen response modifiers (SERMs) such as tamoxifen, raloxifene (EVISTA (Eli Lilly)), and toremifene (FARESTON (Orion Pharmaceutical)), and estrogen receptor downregulators (ERDs), such as fulvestrant (FASLODEX (Astra-Zeneca).

A preferred formulation for use in pharmaceutical compositions of the present invention is complexing the peptide or mimetic thereof or Y-Z or Q-Y-Z composition with a lipid. Also preferred as a formulation is encapsulation of the peptide or mimetic thereof or Y-Z or Q-Y-Z composition or mimetic thereof in a phospholipid vesicle such as, but not limited to, a liposome. Liposomes containing the peptide or mimetic thereof or Y-Z or Q-Y-Z composition or mimetic thereof of the present invention can be prepared in accordance with any of the well known methods such as described by Epstein et al. (Proc. Natl. Acad. Sci. USA 82: 3688-3692 (1985)), Hwang et al. (Proc. Natl. Acad. Sci. USA 77: 4030-4034 (1980)), EP 52,322, EP 36,676; EP 88,046; EP 143,949; EP 142,641; Japanese Pat. Appl. 83-118008, and EP 102,324, as well as U.S. Pat. Nos. 4,485,045 and 4,544,545, the contents of which are hereby incorporated by reference in their entirety. Preferred liposomes are of the small (about 200-800 Angstroms) unilamellar type in which the lipid content is greater than about 10 mol. percent cholesterol, preferably in a range of 10 to 40 mol. percent cholesterol, the selected proportion being adjusted for optimal peptide therapy. However, as will be understood by those of skill in the art upon reading this disclosure, phospholipid vesicles other than liposomes can also be used.

Micelles, nanoparticles, injectable polymer implants, gels and other hydrophilic systems, as well as microemulsions currently used or in development as delivery vehicles for peptides can also be used to formulate pharmaceutical compositions in accordance with the present invention.

Any of these formulations of pharmaceutical compositions may further comprise a targeting agent such as described herein for use in Y-Z or Q-Y-Z composition. When used in this embodiment, the targeting agent is preferably attached to the delivery vehicle (e.g. liposomes, micelles, nanoparticles, injectable polymer implants, gels or other hydrophilic systems).

Another preferred formulation for pharmaceutical compositions of the present invention contains a peptide comprising one or more D amino acids and an aqueous vehicle suitable for intravenous or oral administration. Intravenous formulations expected to be useful as pharmaceutical compositions of the present invention include, but are not limited to, sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, liquid polyethylene glycol, and the like), suitable mixtures thereof, and oils (e.g., vegetable oil). The proper fluidity can be maintained, for example, by the use of a coating such as lecithin, by the maintenance of the required particle size in the case of dispersion, and by the use of surfactants.

Prevention of the action of microorganisms can be achieved by various antibacterial and antifungal agents, for example, parabens, chlorobutanol, phenol, ascorbic acid, thimerosal, and the like. In some cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the peptide of the present invention in the required amount in an appropriate solvent with one or a combination of ingredients enumerated above, as required, followed by filter sterilization. Generally, dispersions are prepared by incorporating the peptide of the present invention into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient (i.e., the peptide) optionally plus any additional desired ingredient from a previously sterile-filtered solution thereof.

Solid dosage forms for oral administration of a peptide or portion thereof, a Y-Z or Q-Y-Z composition, or a mimetic thereof of the present invention include, but are not limited to, ingestible capsules, tablets, pills, lollipops, powders, granules, elixirs, suspensions, syrups, wafers, buccal tablets, troches, and the like. In such solid dosage forms the peptide or portion thereof, the Y-Z or Q-Y-Z composition, or the mimetic thereof is mixed with at least one inert, pharmaceutically acceptable excipient or diluent or assimilable edible carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof, or incorporated directly into the subject's diet. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The percentage of the peptide or portion thereof, the Y-Z or Q-Y-Z composition, or the mimetic thereof in the pharmaceutical compositions and preparations may, of course, be varied. The amount of the peptide or portion thereof, the Y-Z or Q-Y-Z composition, or the mimetic thereof in such therapeutically useful pharmaceutical compositions is such that a suitable dosage will be obtained.

The solid dosage forms of tablets, dragees, capsules, pills, and granules can be prepared with coatings and shells such as enteric coatings and other coatings well-known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The peptide or portion thereof, the Y-Z or Q-Y-Z composition, or the mimetic thereof can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the peptide or portion thereof, the Y-Z or Q-Y-Z composition, or the mimetic thereof, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, ground nut corn, germ olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Suspensions, in addition to the peptide or portion thereof, the Y-Z or Q-Y-Z composition, or the mimetic thereof, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Pharmaceutical compositions of the present invention can be administered to a patient with cancer to potentiate efficacy of an anticancer drug co-administered therewith.

By "potentiating efficacy" it is meant that the anticancer drug is more effective at inhibiting proliferation and/or killing cancer cells in the presence of the ankyrin repeat-like motif peptide or portion thereof, the Y-Z or Q-Y-Z composition, or the mimetic thereof than in the absence of the ankyrin repeat-like motif peptide or portion thereof, the Y-Z or Q-Y-Z composition, or the mimetic thereof.

Pharmaceutical compositions of the present invention can also be administered alone or in combination with a second anticancer agent to inhibit tumorigenesis and/or cancer cell proliferation.

Co-administration with a second anticancer drug or agent is expected to improve efficacy of the second anticancer drug, thereby allowing for decreased doses of the second anticancer drug. This decrease in dose is expected to reduce unwanted side effects of the second anticancer agent.

By "inhibit", "inhibiting" or "inhibition" of tumorigenesis and/or cell proliferation as used herein, it is meant to encompass prevention of tumorigenesis and/or cancer cell proliferation, regression and/or reduction in tumor size and/or a decrease in cancer cell proliferation and well as inhibition and/or prevention of further tumorigenesis and/or cancer cell proliferation.

By "in combination" it is meant to include administration of a single pharmaceutical formulation comprising both the peptide or portion thereof, Y-Z or Q-Y-Z composition or mimetic thereof of the present invention and the anticancer drug as well as administration of two separate pharmaceutical compositions, one comprising the anticancer drug and the other comprising the peptide or portion thereof, Y-Z or Q-Y-Z composition or mimetic thereof of the present invention. When administered separately, the anticancer drug and the peptide or portion thereof, Y-Z or Q-Y-Z composition or mimetic thereof of the present invention can be administered at the same time or at different times.

Accordingly, the pharmaceutical compositions of the present invention are useful in treating cancer. For purposes of the present invention, by "treatment" or "treating" it is meant to encompass all means for controlling cancer by reducing growth of cancer cells and improving response to anticancer drugs. Thus, by "treatment" or "treating" it is meant to inhibit the survival and/or growth of cancer cells, prevent the survival and/or growth of cancer cells, decrease the invasiveness of cancer cells, decrease the progression of cancer cells, decrease the metastases of cancer cells, increase the regression of cancer cells exhibiting a malignant cell phenotype, and/or facilitate the killing of cancer. "Treatment" or "treating" is also meant to encompass maintenance of cancer cells in a dormant state at their primary site as well as secondary sites. Further, by "treating or "treatment" it is meant to increase the efficacy as well as prevent or decrease resistance to other anticancer drugs.

Pharmaceutical compositions may be administered by various routes including, but not limited to, orally, intravenously, intramuscularly, intraperitoneally, subcutaneously, topically, rectally, dermally, sublingually, buccally, intranasally or via inhalation. For at least oral administration, it may be preferred to administer a composition comprising a peptide with one or more D amino acids. The formulation and route of administration as well as the dose and frequency of administration can be selected routinely by those skilled in the art based upon the severity of the condition being treated, as well as patient-specific factors such as age, weight and the like.

Pharmaceutical compositions of the present invention may further comprise a second anticancer drug. Preferably the second anticancer drug is a microtubule inhibitor or a hormonal cancer therapy.

The following nonlimiting examples are provided to further illustrate the present invention.

EXAMPLES

Example 1

Cloning, Expression and Purification of SNCG

The SNCG coding region was amplified from the human cDNA clone (Genbank accession number AF017256) using primers 5' GCGGATCCATGGATGTCTTCAAGAAGGGC-3' (sense; SEQ ID NO:12) and 5' GAGCGGCCGCAGTCTC-CCCCACTCTGGGCCTC 3' (anti-sense; SEQ ID NO:13), and was subsequently subcloned as a BamH1-Not1 fragment into the pGEX-4T-3 vector (Amersham Biosciences) in the correct reading frame to express GST-SNCG fusion protein.

Recombinant GST-SNCG was expressed in *Escherichia coli* BL21 (DE3). Cells were grown in Terrific Broth (Bioshop Inc., Canada) medium and induced with isopropyl-β-D-thiogalacto-pyranoside. Cells were lysed in PBS buffer using a cell disrupter (Cell Disruption System, UK) at 25 kPsi. Clear lysate was loaded on a GSTrap column (Amersham Biosciences). After multiple washes with PBS, in-column cleavage of the GST-tag was performed using thrombin (Sigma). SNCG was eluted with PBS and further purified using HiLoad 16/60 G-200 gel filtration column on AKTA FPLC (Amersham Biosciences). In separate experiments, GST-SNCG was eluted from the column using 10 mM reduced glutathione in PBS and further purified using HiLoad 16/60 G-200 gel filtration column on AKTA FPLC. Peak fractions were pooled and concentrated in PBS buffer. Protein was extensively dialyzed into 10 mM $Na_2HPO_4$—NaOH (pH 7.0) and stored at 4° C. Quantification of GST-SNCG concentration was performed using Bradford reagent (BIORAD) and compared to a bovine serum albumin standard curve. SNCG concentration was determined spectrophotometrically. Purity of GST-SNCG and SNCG was analyzed using 12% SDS-PAGE. The average yield was approximately 22 mg of GST-SNCG and 10 mg of pure SNCG per liter of *E. coli* culture.

Example 2

Ankyrin Repeat-like Peptide Synthesis

Peptide was synthesized by solid phase synthesis with amino-terminal acetylation and carboxyl-terminal amidation to mimic the intact protein at the Protein Function and Discovery Facility at Queen's University, Kingston, Ontario. Peptide was purified by reverse phase HPLC using a C18 column (Vydac, Hesperia, Calif.) and lyophilized. The molecular mass of the peptide was verified by matrix-assisted laser desorption ionization time-of-flight (MALDI-TOF) mass spectrometry. Fifty μL aliquots of 1.2 mM ANK peptide in 10 mM sodium phosphate buffer pH 7.0 were stored at −20° C. until use.

Example 3

Nuclear Magnetic Resonance (NMR)

Isotopically labeled SNCG was expressed in M9 minimal media containing 1 g/l $^{15}N$-ammonium chloride and purified as described above. Final NMR samples were in 10 mM sodium phosphate, pH 7.0, 7.5% $D_2O$. $^1H$-$^{15}N$ heteronuclear single quantum coherence (HSQC) experiments were performed on a Varian Inova 800 MHz spectrometer and processed using NMRPipe (Delaglio et al. J. Biomol. NMR 1995 6:277-293). Results are shown in FIG. 1A.

Example 4

Circular Dichroism (CD) and Fluorescence Spectroscopy

The SNCG-ANK interaction was monitored using far-UV CD recorded on a rapid-scanning monochromator fitted with a CD module (RSM 1000, Olis Inc., Bogart Ga.). Samples containing 0.145 mg/ml SNCG were dialyzed into 5 mM sodium phosphate buffer, pH 7.0 for data acquisition. Spectra were averaged from 12 scans recorded at 25° C. The baseline was corrected by subtracting the spectra measured under identical conditions for the remaining buffer after dialysis. Peptide was reconstituted into flow-through buffer after dialysis and used for titration. Molar ellipticity [θ] was calculated according to the formula $[\theta]=[\theta]\times 100/(nlc)$, where n represents the number of amino acids in the protein, l represents the path length of the cuvette in centimeters and c represents the concentration in millimolar. Percentage secondary structure was calculated using the web-based program CDNN (Bohm et al. Protein Eng. 1992 5:191-195). Results are shown in FIG. 1B and FIG. 1C.

Intrinsic tyrosine fluorescence was measured at 22° C. in a quartz cuvette using an LS50B fluorescence spectrometer (Perkin-Elmer). A 30 μM sample of SNCG (in 10 mM sodium phosphate, pH 7.0) was irradiated at an excitation wavelength of 274 nm and emission spectra were measured from 260-450 nm. The excitation and emission slit widths were set at 5 nm. Varying concentrations of ANK peptide were added to the protein sample and the resultant emission spectra were recorded as described above. A minimum of 6 scans were averaged for each titration point. An averaged scan of peptide in 10 mM sodium phosphate buffer, pH 7.0 and only buffer was used to correct all spectra. For ANS binding experiments samples were excited at 390 nm and emission was measured at 400-600 nm using excitation and emission and slit width of 5 nm. All data was analyzed and deconvoluted using Origin 5.0 (Microcal Inc.).

To understand the molecular mechanism of the SNCG-ANK interaction, the phase diagram method (or method of the parametric dependencies) was applied (See FIG. 2B). The phase diagram method analysis of spectroscopic data is extremely sensitive for the detection of intermediate states (Kuznetsova et al. J. Proteome. Res. 2004 3:485-494) and can be applied to both equilibrium and kinetic data.

The phase diagram method involves building up the diagram of $I_{\lambda,1}$ versus $I_{\lambda,2}$, where $I_{\lambda,1}$ and $I_{\lambda,2}$ are the spectral intensity values measured on wavelengths $\lambda_1$ and $\lambda_2$ under the different experimental conditions for a protein undergoing structural transformations. As spectral intensity is the extensive parameter, it will describe any two-component system by a simple relationship:

$$I(\lambda)=\alpha_1 I_1(\lambda)+\alpha_2 I_2(\lambda)$$
$$\alpha_1+\alpha_2=1, \qquad (1)$$

where $I_1(\lambda)$ and $I_2(\lambda)$ are the spectral intensities corresponding to the first and second components, whereas $\alpha_1$ and $\alpha_2$ are relative contents of these components in a system. Excluding $\alpha_1$ ($\alpha_1=1-\alpha_2$), the equation (1) could be rewritten as:

$$I(\lambda)=(1-\alpha_2)I_1(\lambda)+\alpha_2 I_2(\lambda)=I_1(\lambda)+\alpha_2(I_2(\lambda)-I_1(\lambda)) \qquad (2)$$

It is obvious that $\alpha_2$ may be determined from the spectral intensity measurements at two different wavelengths, $\lambda_1$ and $\lambda_2$. In fact:

$$I(\lambda_1) = I_1(\lambda_1) + \alpha_2(I_2(\lambda_1) - I_1(\lambda_1)) \quad (3)$$

$$I(\lambda_2) = I_1(\lambda_2) + \alpha_2(I_2(\lambda_2) - I_1(\lambda_2)) \quad (4)$$

and $$\alpha_2 = \frac{I(\lambda_2) - I_1(\lambda_2)}{I_2(\lambda_2) - I_1(\lambda_2)} \quad (5)$$

This allows determination of the relationship between $I(\lambda_1)$ and $I(\lambda_2)$ by the substitution of $\alpha_2$ in (3) from (5)

$$I(\lambda_1) = I_1(\lambda_1) + \frac{I(\lambda_2) - I_1(\lambda_2)}{I_2(\lambda_2) - I_1(\lambda_2)}(I_2(\lambda_1) - I_1(\lambda_1)) = \quad (6)$$

$$I_1(\lambda_1) - \frac{I_2(\lambda_1) - I_1(\lambda_1)}{I_2(\lambda_2) - I_1(\lambda_2)}I_1(\lambda_2) + \frac{I_2(\lambda_1) - I_1(\lambda_1)}{I_2(\lambda_2) - I_1(\lambda_2)}I(\lambda_2)$$

or:

$$I(\lambda_1) + a + bI(\lambda_2), \quad (7)$$

where $$a = I_1(\lambda_1) - \frac{I_2(\lambda_1) - I_1(\lambda_1)}{I_2(\lambda_2) - I_1(\lambda_2)}I_1(\lambda_2) \text{ and } b = \frac{I_2(\lambda_1) - I_1(\lambda_1)}{I_2(\lambda_2) - I_1(\lambda_2)} \quad (8)$$

Figure 2:
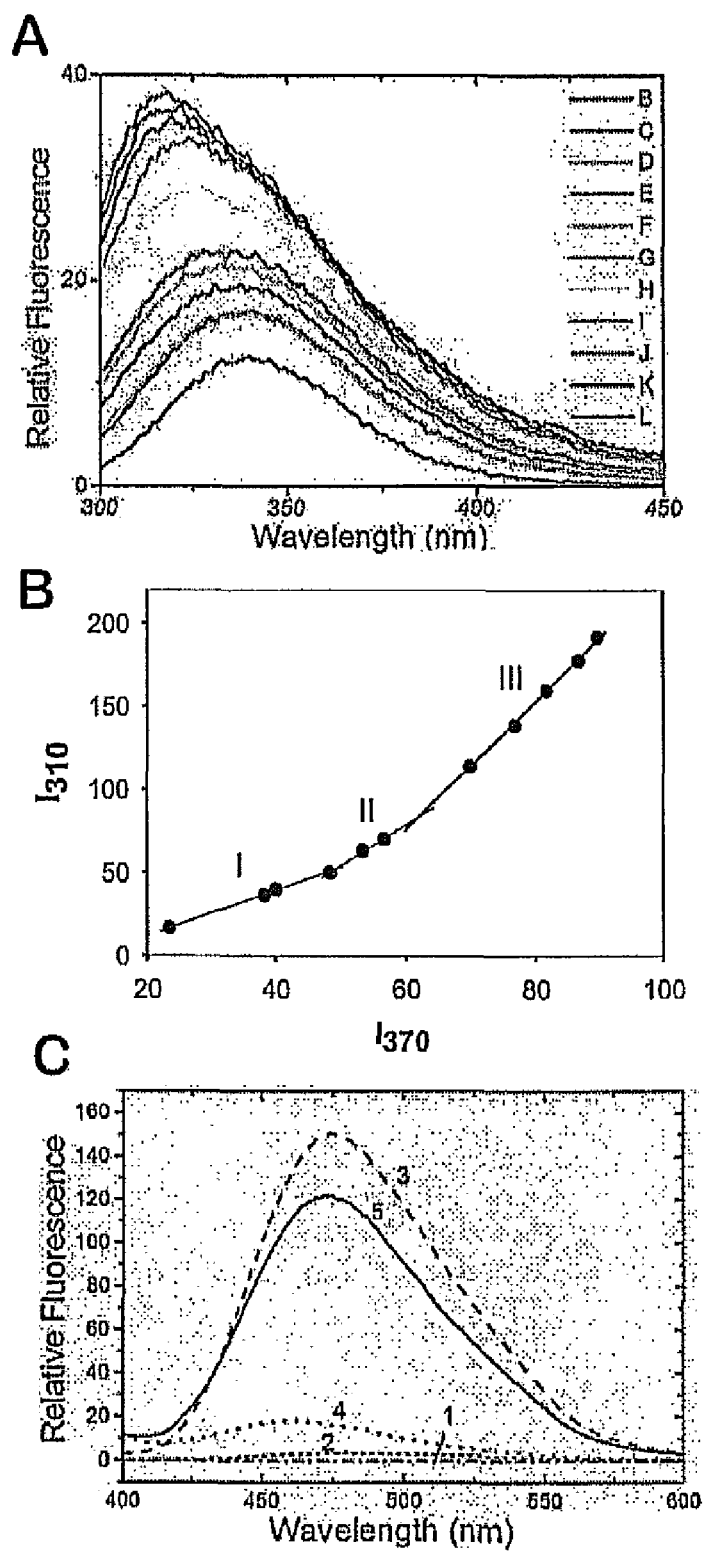
FIGS. 2A through 2C demonstrate the interaction of ANK peptide KGNSALHVASQHGHLGCIQTLVRYGAN- VTMQNHG (SEQ ID NO:1) with SNCG.

The relationship (7) predicts that the dependence $I(\lambda_1) = f(I(\lambda_2))$ will be linear if changes in protein environment lead to the all-or-none transition between two different conformations. On the contrary, the non-linearity of this function reflects the sequential character of structural transformations. Furthermore, each linear portion of the $I(\lambda_1) = f(I(\lambda_2))$ dependence describes the individual all-or-none transition (Kuznetsova et al. J. Proteome. Res. 2004 3:678). Results are shown in FIG. 2.

Example 5

Surface Plasmon Resonance (SPR) and Isothermal Titration Calorimetry (ITC)

The binding interaction between the ANK peptide and GST-SNCG was examined in real time using a BIACORE 3000 biosensor system (Biacore Inc., NJ). Because of the relatively large amount required in this experiment, GST-SNCG, which expresses at least 2 times better than SNCG, was used. A control using GST as the analyte was performed to verify that it did not interact with the peptide. The changes in the refractive index at the sensor chip surface with respect to time are scaled in resonance units (RU). For proteins, every 1000 RU corresponds to a surface mass change of ~1 ng/mm². All experiments were performed at 25° C. using research grade carboxymethylated dextran matrix (CM5) sensor chips (Biacore Inc.). Bulk refractive index changes, non-specific binding, and instrument drift were corrected for by on-line subtraction (response over active surface less response over reference surface). Prior to all analyses the GST-SNCG and ANK peptide preparations were dialyzed against the running buffer to minimize bulk effects. Blank analyte injections (running buffer only) were subtracted from the specific binding isotherms to further minimize instrument noise. Results are shown in FIG. 3A.

For the affinity binding experiments, active flow cells of approximately 5000 RU ANK peptide (288 µg/mL in 10 mM sodium phosphate buffer, pH 7.0) were immobilized using the ligand thiolcoupling kit (Biacore, Inc.) and running buffer 1 (10 mM HEPES, 150 mM NaCl, 3.4 mM EDTA, 0.005% (v/v) P20 surfactant, pH 7.4). For kinetic binding experiments, active flow cells of approximately 300 RU ANK peptide were immobilized in a similar manner. For reference flow cells, the surfaces were activated and blocked in a similar manner but in the absence of any ligand addition. In all cases the analyte binding measurements were performed using running buffer 2 (running buffer 1 plus 0.1% P20 surfactant). Following each binding interaction, surfaces were regenerated using running buffer 1 containing 20 mM ε-ACA/1 M NaCl/0.1% P20 surfactant. Typical parameters for each cycle of the affinity and kinetic binding methods were as follows: 60 µL of analyte (with 600 seconds of dissociation) at 10 µL/minute, 10×60 µL of regeneration at 20 µL/minute, 250 µL of running buffer at 10 µL/minute. Data was analyzed using BIAevaluation 3.1 software (Biacore Inc.). The data was analyzed globally, using a simultaneous fit for both association ($k_a$, $M^{-1}s^{-1}$) and dissociation ($k_d$, $s^{-1}$). The KD (M) value was calculated as $k_d/k_a$.

Titration calorimetry measurements were performed with a VP-ITC calorimeter (Microcal, Northampton, Mass.). The protein solution for ITC was dialyzed extensively overnight against 10 mM phosphate buffer, pH 7.0. The peptide solution was prepared by diluting with the buffer used for the protein dialysis. Injections (6 µl×50) of peptide (400 µM) were done by means of a rotating stirrer-syringe to the reaction cell, containing 1.43 ml of the 50 µM protein solution. The heat of dilution was determined to be negligible in separate titrations of the ligand into the buffer solution. Calorimetric data analysis was carried out with ORIGIN 5.0 software (MicroCal). Binding parameters such as the number of binding sites, the binding constant, and the binding enthalpy of bound ligand were determined by fitting the experimental binding isotherms. Results are shown in FIG. 3B.

Example 6

Microinjection of ANK and Immunofluorescence Microscopy

MCF7-SNCG and MCF-Neo were grown to 80% confluence, split with trypsin and seeded on a 22 mm glass coverslip treated with human fibronectin (10 mg/ml) into 60 mm diameter dishes containing cell maintenance medium for 24 hours and utilized for the experiments. In initial experiments ANK peptide (5, 10 or 100 µM) was microinjected. In all further experiment to date, ANK peptide (10 µM), together with goat IgG (1 mg/ml) and fluoroscein isothiocyanate (FITC, 5 mg/ml; Molecular Probes) into the MCF7-SNCG or MCF7-Neo cells under a 40× magnification of phase contrast microscope (Carl Zeiss Inc.) using a pressure injection system (Femtojet, Eppendorf). To exclude the possibility that microinjection might affect cell cycle and proliferation, MCF7-Neo and MCF7-SNCG were microinjected with goat IgG as a control. Injections were done at a constant flow setup by varying the injection pressure Pc between 40-70 units. The microscope stage was kept at 37° C. using thermal control device (Tempcontrol-37-2 Digital). Approximately 25-30 cells were microinjected in each experiment (n=3). Cells were quickly incubated to revive. Thirty minutes after microinjection, the coverslips were transferred to medium containing 0.5 µM nocodazole and incubated for an additional 24 hours. Medium without nocodazole was used for control. Results are shown in FIG. 4A.

For the immunofluorescence experiments, cells were fixed in 0.5% buffered paraformaldehyde for 8 minutes at room temperature. After permeabilization with 0.2% TritonX-100 in PBS, the fixed cells were blocked with 3% bovine serum albumin (BSA) in phosphate buffered saline (PBS) for overnight at 4° C. To detect goat IgG which is an injection marker, the cells were incubated with Alexa488-conjugated donkey anti-goat IgG secondary antibodies (1:500; Molecular Probes) in blocking solution for 1 hour at room temperature. After washing, the cover slips containing the immunolabeled cells were treated with 40 µM DAPI for 10 minutes before washing and mounting with an antifade mounting medium (Biomeda Gel mount, Electron Microscopy Sciences). Cells were observed via two photon excitation microscopy using a confocal inverted microscope (Leica TCS SP2 MP) at ×100 objective (oil). Cells were scored by identifying cells containing Alexa Fluor 488 excited at 488 nm, and the emission measured at 500-535 nm; DAPI was excited at 345 nm and the emission was measured at 445 nm. Images were captured sequentially to minimize signal overlapping, and were processed and merged using PhotoShop (Adobe, San Jose, Calif.). Mitotic index was determined as described by Gupta et al. (Oncogene 2003 22:7593-7599) and Inaba et al. Breast Cancer Res. Treat. 2005 94:25-35). Results are shown in FIG. 4B.

Example 7

Cloning and Expression of PEGFP-ANK

The sense sequence of the 105 bp single-stranded oligonucleotide corresponding to the AA sequence of the ANK peptide with a stop codon was as follows: aag ggc aac agt gcc ctt cac gta gcc tca cag cat ggc cac ctt gga tgc ata cag acc ttg gtt aga tat gga gca aat gtc acc atg cag aac cac ggg tga (SEQ ID NO:14). This single stranded oligonucleotide was synthesized by Qiagen Inc. (Valencia, Calif.) and used as the template in a PCR reaction to produce a double stranded DNA fragment with the 5' primer ANK-F (aagggcaacagtgcccttc (SEQ ID NO:15)) and the 3' primer ANK-R (tcacccgtggttct-gcatg (SEQ ID NO:16)). The DNA fragment was directly cloned into pCR 2.1-TOPO vector. The insert was released from the TOPO vector by EcoR1 digestion and cloned into the EcoR1 site of an expression vector pEGFP-C2 to produce an EGFP-ANK fusion protein. The resulting plasmid pEGFP-ANK was sequenced to verify the correct inframe ligation and right orientation of the peptide. Cytoplasmic expression of EGFP-ANK fusion protein was confirmed by green fluorescent signals in cells transfected with PEGFP-ANK. The correct molecular mass of EGFP-ANK was verified by western blotting with anti-GFP antibody. Results are shown in FIG. 5A.

Example 8

Detection of ANK-SNCG Interaction in vivo

MCF7-neo and MCF7-SNCG clones were transfected with pEGFP-ANK plasmid or the control plasmid pEGFP by FuGENE 6 transfection reagent (Roche). Two days after transfection, cells were lysed in RIPA buffer [150 mM NaCl, 50 mM Tris-HCl (pH 8.0), 1% NP-40, and 0.5% sodium deoxycholate] in the presence of protease inhibitors. Cell lysate containing 2 mg of protein was precleared with 100 µl of protein A sepharose (50% slurry) for 10 minute at 4° C. and then incubated with 10 µg of goat anti-SNCG antibody at 4° C. for 3 hours. Thirty microliters of protein A sepharose was then added to the lysate and the mixture was diluted with equal volume of 2×IP buffer IP buffer [1% Triton X-100, 10 mM Tris pH 7.4, 0.5% NP-40, 150 mM NaCl, 1 mM EDTA, 1 mM EGTA pH 8.0] containing protease inhibitor cocktail. The mixture was further incubated at 4° C. overnight. After centrifugation, the sepharose beads were resuspended in TB buffer (50 mM Tris, 150 mM NaCl, pH. 7.0). After 10 washes by TB buffer, proteins bound to the beads were eluted with 2× sodium dodecyl sulphate (SDS) sample buffer by boiling. Proteins in supernatants were separated by SDSPAGE, and analyzed by western blotting with 1:100 dilution of a goat anti-SNCG polyclonal antibody (Santa Cruz, sc-10698, 1:200 dilution) and subsequently probed with a monoclonal anti-GFP antibody (Santa Cruz, sc-9996, 1:500 dilution). Results are shown in FIG. 5C.

Example 9

Detection of BubR1-SNCG Interaction in the Absence and Presence of ANK Peptide

COS7 cells were co-transfected with pCS2-BubR1 ((Gupta et al. Oncogene 2003 22:7593-7599; Inaba et al. Breast Cancer Res. Treat. 2005 94:25-35), pCI-SNCG, and pEGFP-ANK plasmid or with the control plasmid pEGFP by FuGENE 6 transfection reagent (Roche). Two days after transfection, cells were lysed and IP with anti-SNCG antibody was performed as described in Example 8. The proteins in IP complexes and total cell lysates were analyzed by western blotting using a monoclonal anti-Myc antibody (BD Biosciences, 631206, 1:500 dilution), anti-GFP antibody, and anti-SNCG antibody. Results are shown in FIG. 6.

Example 10

Determination of Mitotic Index in MCF7-SNCG Cell in Presence and Absence of EGFP-ANK Cells (MCF7-SNCG transfected with EGFP-ANK or EGFP control vector) grown on 13-mm round-glass coverslips inserted in wells of 24 well-culture plates were untreated or treated with anti-microtubule drug paclitaxel (TAXOL) at 0.5 µM concentration for 36 hours. Thereafter cells were fixed with 100% methanol for 20 minutes at −20° C. and then stained with 1 µg/ml of DAPI. For each sample, 200-300 cells randomly chosen from 5 different views under a Nikon fluorescent microscope were scored for interphase, mitotic, or apoptotic based upon nuclei morphology. Available bar graph (FIG. 7) shows that the expression of EGFP-ANK disrupts the SNCG-mediated inhibition of mitotic checkpoint function.

The data shown were derived from three separate transfections.

Example 11

Design, Cloning and Expression of pEGFP-ANK Deletion Peptides

Deletion peptides of EGFP-ANK were designed based on a molecular model of ANK peptide generated using an online webserver swissmodel with the extension expasy.org/. Deletion peptides designed were amplified by PCR, followed by directional cloning into the EcoR I site of EGFP—C2 to produce EGFP-ANK deletion peptides. The resulting plasmid PEGFP-ANK was sequenced to verify the correct inframe ligation and right orientation of the peptide. Cytoplasmic expression of EGFP-ANK deletion peptide was confirmed by green fluorescent signals in cells transfected with pEGFP-ANK deletion peptides. The correct molecular mass of EGFP-ANK was verified by western blotting with anti-GFP antibody.

Deletion peptide sequences followed by primers designed for cloning are depicted below:

```
P13
CACCTTGGATGCATACAGACCTTGGTTAGATATGGAGCATGA    (SEQ ID NO: 17)
 H  L  G  C  I  Q  T  L  V  R  Y  G  A  *     (SEQ ID NO: 4)

Primer P13for - CACCTTGGATGCATACAG             (SEQ ID NO: 18)

Primer P13rev - TCATGCTCCATATCTAACC            (SEQ ID NO: 19)

P18
CTTCACGTAGCCTCACAGCATGGCCACCTTGGATGCATACAGACCTTGGTTAGATGA  (SEQ ID NO: 20)
 L  H  V  A  S  Q  H  G  H  L  G  C  I  Q  T  L  V  R  *   (SEQ ID NO: 3)

Primer P18for - CTTCACGTAGCCTCACAGC            (SEQ ID NO: 21)

Primer P18rev - TCATCTAACCAAGGTCTG             (SEQ ID NO: 22)

P12
GGCAACAGTGCCCTTCACGTAGCCTCACAGCATGGCTGA        (SEQ ID NO: 23)
 G  N  S  A  L  H  V  A  S  Q  H  G  *         (SEQ ID NO: 2)

Primer P12for - CTTCACGTAGCCTCACAGC            (SEQ ID NO: 24)

Primer P12rev - TCAGCCATGCTGTGAGGC             (SEQ ID NO: 25)

P8
GGAGCAAATGTCACCATGCAGAACTGA                    (SEQ ID NO: 26)
 G  A  N  V  T  M  Q  N  *                     (SEQ ID NO: 5)

Primer P8for - aattGGAGCAAATGTCACCATGCAGAACTGA (SEQ ID NO: 27)

Primer P8rev - aattTCAGTTCTGCATGGTGACATTTGCTCC (SEQ ID NO: 28)
```

MCF7-neo and MCF7-SNCG clones were transfected with pEGFP-ANK deletion peptides P8, P12, P13, P18 plasmid or the control plasmid pEGFP by FuGENE 6 transfection reagent (Roche). Two days after transfection, cells were lysed in RIPA buffer [150 mM NaCl, 50 mM Tris-HCl (pH 8.0), 1% NP-40, and 0.5% sodium deoxycholate] in the presence of protease inhibitors. Cell lysate containing 2 mg of protein was precleared with 100 µl of protein A sepharose (50% slurry) for 10 min at 4° C. and then incubated with 10 µg of goat anti-SNCG antibody at 4° C. for 3 h. Thirty-µl of protein A sepharose was then added to the lysate and the mixture was diluted with equal volume of 2×IP buffer. The mixture was further incubated at 4° C. overnight. After centrifugation, the sepharose beads were resuspended in TB buffer (50 mM Tris, 150 mM NaCl, pH. 7.0). After 10 washes by TB buffer, proteins bound to the beads were eluted with 2×SDS sample buffer by boiling. Proteins in supernatants were separated by SDS-PAGE, and analyzed by western blotting with 1:100 dilution of anti-SNCG antibody (1:200 dilution, sc-10698, Santa Cruz, Calif.) and subsequently probed with anti-GFP mAb (1:500 dilution, sc-9996, Santa Cruz, Calif.).

Example 12

Detection of ANK-SNCG Interaction and Mitotic Index in Breast Cancer Cell Lines T47D, MCF7-neo and MCF7-SNCG clones were transfected with pEGFP-ANK plasmid or the control plasmid PEGFP by FuGENE 6 transfection reagent (Roche (Indianapolis, Ind.). Cell lysate was prepared as described by Gupta et al. (Oncogene 2003 22(7):595-599) and Zhou et al. (Int. J. Oncol. 2006 29:289-295) followed by co-immunoprecipitation using 10 µg of goat anti-SNCG antibody. Western blotting was performed with a monoclonal anti-GFP antibody (Santa Cruz Biotechnology, Santa Cruz, Calif.), sc-9996, 1:500 dilution) and then subsequently probed with 1:100 dilution of a goat anti-SNCG polyclonal antibody (Santa Cruz, sc-10698). The mitotic index was determined followed by the treatment with 0.5 µM paclitaxel as per standard protocol (Gupta et al. Oncogene 2003 22(7):595-599).

Example 13

GST Pull-Down Assay

GST-SNCG (20 µg) protein or GST alone was added to a pre-equilibrated slurry of glutathione-sepharose 4B and incubated for 60 minutes. The unbound protein was then washed three times with PBS containing 1% Triton X-100. MCF-7 cell lysate (1 mg) was mixed with the beads and incubated for 1 hour at 4° C. After extensive washes, the beads were collected, boiled in sample buffer, separated on 12% SDS gel and analyzed by western blotting. Western blotting was performed with a monoclonal anti-GFP antibody (Santa Cruz Biotechnology, Santa Cruz, Calif.), sc-9996, 1:500 dilution) and then subsequently probed with 1:100 dilution of a goat anti-SNCG polyclonal antibody (Santa Cruz, sc-10698).

Example 14

Immunostaining of Phosphorylated Histone (H3)

The MCF7-SNCG and MCF7-neo cells cultured on coverslips were transfected by pEGFP or PEGFP-ANK respectively for more than 24 hours and treated with 0.5 µM paclitaxel (Sigma, St. Louis, Mo.) for 18 hours. The mitotic index was calculated according to the proportion of the number of $H^3$ staining GFP positive cells to total GFP positive cells.

Example 15

Flow Cytometry

MCF7-SNCG cells were cultured using standard techniques, transfected with FuGENE 6 (Roche), and fixed using chilled EtOH, followed by probing with 2 µg/ml rabbit polyclonal anti-phospho-H3 (Ser10, Upstate, Charlottesville, Va.) at room temperature. After two washes with PBS, cells were treated with APC-labeled goat anti-rabbit secondary antibody (Molecular Probes, Carlsbad, Calif.), 50 µg/ml propidium iodide (PI) and 100 µg/ml RNase. Cells were analyzed for cell cycle and anti-phospho-H3 population on a FACSCalibur flow cytometer using CellQuest software (Becton Dickinson, San Jose, Calif.). The mitotic index was calculated according to the proportion of the number of double $H^3$-GFP positive cells to the total GFP positive cells.

What is claimed is:

1. A synthetic peptide or a mimetic thereof, said synthetic peptide consisting of $GX_1X_2X_3LHX_4AX_5X_6X_7GHX_8X_9X_{10}X_{11}X_{12}X_{13}LX_{14}X_{15}X_{16}GA$ (SEQ ID NO:7) or $GX_1X_2X_3LHX_4AX_5X_6X_7GHX_8X_9X_{10}X_{11}X_{12}X_{13}LX_{14}X_{15}X_{16}GAX_{17}X_{18}NX_{19}X_{20}X_{21}X_{22}$ (SEQ ID NO:32), where $X_1$ is B1 or N; $X_2$ is B2; $X_3$ is B1; $X_4$ is B1 or Q; $X_5$ is B1 or B2; $X_6$ is B2 or K; $X_7$ is B2 or V; $X_8$ is B1 or K; $X_9$ is B3 or B4; $X_{10}$ is I or C; $X_{11}$ is B1; $X_{12}$ is B1, B2 or R; $X_{13}$ is B1 or B4; $X_{14}$ is B1 or T; $X_{15}$ is B2, B3 or R; $X_{16}$ is B1, B2 or E; $X_{17}$ is B1, B2 or E; $X_{18}$ is B1, B2 or D; $X_{19}$ is B1 or B2; $X_{20}$ is B1 or B3; $X_{21}$ is B1 or B2; $X_{22}$ is B1, B2 or E; B1 is G, A, V, L, I, M, F, W, or P; B2 is S, T, C, Y, N, or Q; B3 is D or E; and B4 is K, R or H; or a portion thereof, or SEQ ID NO: 1, 8, 9, 10 or 11 or a portion thereof.

2. The synthetic peptide or mimetic thereof of claim 1 wherein the amino acid sequence of said synthetic peptide comprises SEQ ID NO: 1, 2 or 5.

3. A composition having a formula:
Y-Z
wherein Y comprises a peptide or a mimetic thereof of claim 2; and
wherein Z comprises a compound linked to Y that enhances the performance of Y.

4. The composition of claim 3 wherein Z comprises a targeting agent, a second agent for treatment of cancer, an agent which enhances solubility, absorption, distribution, half-life, bioavailability, stability, activity and/or efficacy, or an agent which reduces toxicity or side effects of the composition.

5. A pharmaceutical composition comprising a synthetic peptide consisting of SEQ ID NO:1 or SEQ ID NO:2 or a mimetic thereof and a pharmaceutically acceptable vehicle.

6. The pharmaceutical composition of claim 5 further comprising a second agent for treatment of cancer.

7. The pharmaceutical composition of claim 5 wherein the synthetic peptide or mimetic thereof or the composition is complexed with a lipid.

8. The pharmaceutical composition of claim 5 wherein the synthetic peptide or mimetic thereof or the composition is enclosed in a phospholipid vesicle.

9. A method for potentiating efficacy of an anticancer drug at treating cancer in a patient comprising administering to the patient the pharmaceutical composition of claim 5.

10. A method for potentiating efficacy of an anticancer drug at treating cancer in a patient comprising administering to the patient the pharmaceutical composition of claim 5 and a second anticancer agent.

11. The method of claim 9 wherein the cancer comprises cancer cells expressing SNCG.

12. The method of claim 9 wherein the anticancer drug is a microtubule inhibitor or a hormonal cancer treatment.

13. A method for treating cancer in a patient suffering from cancer comprising administering to the patient the pharmaceutical composition of claim 5.

14. A method for treating cancer in a patient suffering from cancer comprising administering to the patient the pharmaceutical composition of claim 5 and a second anticancer agent.

15. The method of claim 13 wherein the patient is suffering from a cancer comprising cancer cells expressing SNCG.

16. The method of claim 13 wherein the anticancer drug is a microtubule inhibitor or a hormonal cancer treatment.

* * * * *